(12) United States Patent
Sugahara

(10) Patent No.: US 11,998,378 B2
(45) Date of Patent: Jun. 4, 2024

(54) IMAGE TRANSMISSION APPARATUS, IMAGE TRANSMISSION METHOD, AND IMAGE TRANSMISSION PROGRAM

(71) Applicant: FUJIFILM CORPORATION, Tokyo (JP)

(72) Inventor: Masataka Sugahara, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 341 days.

(21) Appl. No.: 17/467,300

(22) Filed: Sep. 6, 2021

(65) Prior Publication Data
US 2021/0393222 A1 Dec. 23, 2021

Related U.S. Application Data

(63) Continuation of application No. PCT/JP2019/044392, filed on Nov. 12, 2019.

(30) Foreign Application Priority Data

Mar. 26, 2019 (JP) ................................ 2019-057800

(51) Int. Cl.
*A61B 6/46* (2024.01)
*A61B 6/02* (2006.01)
*A61B 6/03* (2006.01)

(52) U.S. Cl.
CPC .............. *A61B 6/463* (2013.01); *A61B 6/025* (2013.01); *A61B 6/032* (2013.01)

(58) Field of Classification Search
CPC ........... A61B 6/02; A61B 6/025; A61B 6/032; A61B 6/463
See application file for complete search history.

(56) References Cited

U.S. PATENT DOCUMENTS

2013/0024208 A1 1/2013 Vining
2015/0213725 A1 7/2015 Huntley et al.
(Continued)

FOREIGN PATENT DOCUMENTS

CN 109857307 A 6/2019
EP 2979638 A1 2/2016
(Continued)

OTHER PUBLICATIONS

English language translation of the following: Office action dated Jun. 28, 2022 from the JPO in a Japanese patent application No. 2021-508714 corresponding to the instant patent application.
(Continued)

*Primary Examiner* — Gerald Johnson
(74) *Attorney, Agent, or Firm* — SOLARIS Intellectual Property Group, PLLC

(57) ABSTRACT

A reconfiguration unit sequentially generates a plurality of tomographic images on each of a plurality of tomographic planes of a subject by reconfiguring a plurality of projection images corresponding to each of a plurality of radiation source positions. A determination unit determines whether or not at least one of the tomographic images is visually recognized by an operator. A transmission unit transmits the plurality of tomographic images to an external apparatus in a case where it is determined that at least one of the tomographic images is visually recognized by the operator.

13 Claims, 15 Drawing Sheets

(56) References Cited

U.S. PATENT DOCUMENTS

| | | | | |
|---|---|---|---|---|
| 2015/0348293 A1* | 12/2015 | Sugahara | ............... | A61B 6/032 |
| | | | | 345/424 |
| 2016/0015333 A1* | 1/2016 | Morita | ................... | A61B 6/502 |
| | | | | 378/22 |
| 2016/0206268 A1* | 7/2016 | Fukuda | ................ | A61B 6/5205 |
| 2019/0282091 A1* | 9/2019 | Matsunobu | .......... | A61B 3/0033 |

FOREIGN PATENT DOCUMENTS

| | | | |
|---|---|---|---|
| JP | 2005-287891 | A | 10/2005 |
| JP | 2006-95054 | A | 4/2006 |
| JP | 2008-237369 | A | 10/2008 |
| JP | 2013-034621 | A | 2/2013 |
| JP | 2014-195622 | A | 10/2014 |

OTHER PUBLICATIONS

English language translation of the following: Office action dated Apr. 5, 2022 from the JPO in a Japanese patent application No. 2021-508714 corresponding to the instant patent application.
Extended European Search Report dated Apr. 21, 2022 issued in corresponding EP Patent Application No. 19920796.0.
International Search Report issued in International Application No. PCT/JP2019/044392 dated Feb. 4, 2020.
Written Opinion of the ISA issued in International Application No. PCT/JP2019/044392 dated Feb. 4, 2020.

* cited by examiner

IMAGE TRANSMISSION APPARATUS, IMAGE TRANSMISSION METHOD, AND IMAGE TRANSMISSION PROGRAM

CROSS-REFERENCE TO RELATED APPLICATIONS

The present application is a Continuation of PCT International Application No. PCT/JP2019/044392, filed on Nov. 12, 2019, which claims priority to Japanese Patent Application No. 2019-057800, filed on Mar. 26, 2019. Each application above is hereby expressly incorporated by reference, in its entirety, into the present application.

BACKGROUND

Technical Field

The present disclosure relates to an image transmission apparatus, an image transmission method, and an image transmission program for transmitting a tomographic image acquired by tomosynthesis imaging to an external apparatus.

Related Art

In recent years, in a radiography apparatus using radiation such as X-rays or gamma-rays, in order to observe a diseased part in more detail, there has been proposed tomosynthesis imaging of performing imaging by moving a radiation source and irradiating a subject with radiation at a plurality of radiation source positions, and generating tomographic images in which desired tomographic planes are highlighted by adding a plurality of projection images acquired by the imaging. In the tomosynthesis imaging, the plurality of projection images are acquired by moving the radiation source in parallel with a radiation detector or so as to draw a circular or an elliptical arc according to characteristics of an imaging apparatus and required tomographic images and imaging the subject at the plurality of radiation source positions, and the tomographic images are generated by reconfiguring the projection images using an inverse projection method such as a simple inverse projection method or a filtering inverse projection method.

The tomographic images are generated on a plurality of tomographic planes of the subject, and thus it is possible to separate structures that are overlapped in a depth direction in which the tomographic planes of the subject are lined up. Therefore, it is possible to find a lesion which is unlikely to be detected in the two-dimensional image acquired by simple imaging in the related art.

On the other hand, the tomographic images generated by tomosynthesis imaging are transmitted from the imaging apparatus to an external apparatus such as an image storage server or an image viewer, and are stored or displayed for diagnosis. Various methods for transmitting the generated tomographic images to the external apparatus have been proposed. For example, JP2014-195622A proposes a method of sequentially displaying the generated tomographic images on a console connected to the imaging apparatus, receiving an input of a transmission instruction after an image quality is confirmed by an operator such as a radiologist, and transmitting the tomographic images from the console to the external apparatus.

On the other hand, various methods for easily transmitting a radiographic image to the external apparatus have been proposed. For example, JP2013-034621A proposes a method of, in a case where imaging of radiographic images is performed a plurality of times, transmitting the radiographic images to the external apparatus without waiting for a transmission instruction from the operator by detecting an instruction to start imaging of the next radiographic image or an occurrence of an event such as display of the radiographic image having a predetermined resolution in a case where the radiographic images having a plurality of resolutions are generated.

On the other hand, the tomographic images acquired by tomosynthesis imaging have large amounts of data because the tomographic images have high resolutions and the number of the tomographic images is large. For this reason, it takes a long time to complete transmission of the tomographic images to the external apparatus. As a result, even in a case where it is desired to immediately display the tomographic images on an image viewer as one external apparatus, since the tomographic images are transmitted to the external apparatus after examination including tomosynthesis imaging is completed or the tomographic images are transmitted to the external apparatus after a transmission instruction from the operator is received, the tomographic images cannot be immediately displayed. Therefore, it is considered to transmit the tomographic images to the external apparatus in order of generation. However, the transmitted tomographic images are images that are not recognized by the operator. Further, in a case where a blur or the like occurs in the tomographic images, after the tomographic images are transmitted, it is necessary to perform imaging again and reconfigure the tomographic images again. However, in a case where imaging is performed again and reconfiguration of the tomographic images is performed again, it is necessary to transmit the tomographic images again.

On the other hand, according to the method described in JP2013-034621A, the radiographic images are transmitted to the external apparatus without waiting for an instruction of the operator. However, the method described in JP2013-034621A does not target images having large amounts of data such as the tomographic images generated by tomosynthesis imaging.

SUMMARY OF THE INVENTION

The present disclosure has been made in view of the above circumstances, and an object of the present disclosure is to reduce a waiting time from a time when imaging is completed to a time when the tomographic images can be read in a case where it is desired to display and read the tomographic images stored in the external apparatus, as compared with a case where examination including tomosynthesis imaging is completed and then the tomographic images are transmitted to the external apparatus or a case where the tomographic images are transmitted to the external apparatus according to an instruction of the operator.

An image transmission apparatus according to an aspect of the present disclosure includes: a reconfiguration unit that sequentially generates a plurality of tomographic images on each of a plurality of tomographic planes of a subject by reconfiguring a plurality of projection images corresponding to each of a plurality of radiation source positions, the plurality of projection images being generated by causing an imaging apparatus to perform tomosynthesis imaging of relatively moving a radiation source with respect to a detection surface of a detection unit and irradiating the subject with radiation at the plurality of radiation source positions according to movement of the radiation source; a determination unit that determines whether or not at least one of the tomographic images is visually recognized by an operator; and a transmission unit that transmits the plurality of tomographic images to an external apparatus in a case where it is determined that at least one of the tomographic images is visually recognized by the operator.

In the image transmission apparatus according to the aspect of the present disclosure, the transmission unit may transmit the plurality of tomographic images to the external apparatus before an instruction of completion of examination including the tomosynthesis imaging is input from the operator or before an instruction of transmission of the plurality of tomographic images to the external apparatus is input from the operator.

In the image transmission apparatus according to the aspect of the present disclosure, in a case where a simple two-dimensional image of the subject is acquired by simply imaging the subject with the same positioning as the tomosynthesis imaging, the transmission unit may transmit the plurality of tomographic images to the external apparatus before an instruction of completion of examination including the tomosynthesis imaging is input from the operator or before an instruction of transmission of the plurality of tomographic images to the external apparatus is input from the operator.

The "simple imaging" is an imaging method of acquiring a single two-dimensional image as a transmissive image of a subject, that is, a simple two-dimensional image by irradiating the subject with radiation once. Further, "the transmission unit transmits the plurality of tomographic images before an instruction of completion of examination including the tomosynthesis imaging is input from the operator or before an instruction of transmission of the plurality of tomographic images to the external apparatus is input from the operator" means that the transmission unit automatically transmits the plurality of tomographic images to the external apparatus even in a case where an instruction of completion of examination including the tomosynthesis imaging is not input from the operator or even in a case where an instruction of transmission of the plurality of tomographic images to the external apparatus is not input from the operator.

The image transmission apparatus according to the aspect of the present disclosure further includes a display control unit that sequentially displays, on a display unit, the tomographic images which are sequentially generated. The determination unit may determine that at least one of the tomographic images is visually recognized by the operator in a case where the display control unit displays the last tomographic image on the display unit.

The "last tomographic image" is a tomographic image which is generated last among the plurality of tomographic images which are sequentially generated. For example, in a case where the tomographic images are sequentially generated from a lower tomographic plane to an upper tomographic plane of the subject, the last tomographic image is a tomographic image on the uppermost tomographic plane. On the other hand, in a case where the tomographic images are sequentially generated from an upper tomographic plane to a lower tomographic plane of the subject, the last tomographic image is a tomographic image on the lowermost tomographic plane.

The image transmission apparatus according to the aspect of the present disclosure further includes a display control unit that sequentially displays, on a display unit, the tomographic images which are sequentially generated. The determination unit may determine that at least one of the tomographic images is visually recognized by the operator in a case where the display control unit displays the last tomographic image on the display unit and displays a predetermined number of the tomographic images on the tomographic planes that are different from the last tomographic image on the display unit according to an instruction of the operator.

In this case, the determination unit may determine that at least one of the tomographic images is visually recognized by the operator in a case where the display control unit displays the predetermined number of the tomographic images on the display unit and then a certain time has passed.

Further, in this case, the determination unit may determine that at least one of the tomographic images is visually recognized by the operator in a case where the display control unit displays the predetermined number of the tomographic images on the display unit and then a predetermined operation is received.

The image transmission apparatus according to the aspect of the present disclosure further includes a display control unit that sequentially displays, on a display unit, the tomographic images which are sequentially generated. The determination unit may determine that at least one of the tomographic images is visually recognized by the operator in a case where the display control unit displays the last tomographic image on the display unit and displays two or more tomographic images among the plurality of tomographic images on the display unit at the same time according to an instruction of the operator.

In this case, the determination unit may determine that at least one of the tomographic images is visually recognized by the operator in a case where the display control unit displays two or more tomographic images among the plurality of tomographic images on the display unit at the same time and then a certain time has passed.

Further, in this case, the determination unit may determine that at least one of the tomographic images is visually recognized by the operator in a case where the display control unit displays two or more tomographic images among the plurality of tomographic images on the display unit at the same time and then a predetermined operation is received.

The image transmission apparatus according to the aspect of the present disclosure further includes: a display control unit that sequentially displays, on a display unit, the tomographic images which are sequentially generated; and a line-of-sight detection unit that detects a line-of-sight of the operator. The determination unit may determine that at least one of the tomographic images is visually recognized by the operator in a case where it is detected that the operator looks at the display unit for a certain time while the tomographic images are being displayed on the display unit.

An image transmission method according to another aspect of the present disclosure includes: sequentially generating a plurality of tomographic images on each of a plurality of tomographic planes of a subject by reconfiguring a plurality of projection images corresponding to each of a plurality of radiation source positions, the plurality of projection images being generated by causing an imaging apparatus to perform tomosynthesis imaging of relatively moving a radiation source with respect to a detection surface of a detection unit and irradiating the subject with radiation at the plurality of radiation source positions according to movement of the radiation source; determining whether or not at least one of the tomographic images is visually recognized by an operator; and transmitting the plurality of tomographic images to an external apparatus in a case where it is determined that at least one of the tomographic images is visually recognized by the operator.

A program causing a computer to execute the image transmission method according to the aspect of the present disclosure may be provided.

An image transmission apparatus according to still another aspect of the present disclosure includes: a memory that stores a command to be executed by a computer; and a processor configured to execute the stored command. The processor is configured to execute: processing of sequentially generating a plurality of tomographic images on each of a plurality of tomographic planes of a subject by reconfiguring a plurality of projection images corresponding to each of a plurality of radiation source positions, the plurality of projection images being generated by causing an imaging apparatus to perform tomosynthesis imaging of relatively moving a radiation source with respect to a detection surface of a detection unit and irradiating the subject with radiation at the plurality of radiation source positions according to movement of the radiation source; processing of determining whether or not at least one of the tomographic images is visually recognized by an operator; and processing of transmitting the plurality of tomographic images to an external apparatus in a case where it is determined that at least one of the tomographic images is visually recognized by the operator.

According to the present disclosure, in a case where it is desired to display and read the transmitted tomographic images in the external apparatus, it is possible to reduce a waiting time from a time when imaging is completed to a time when the tomographic images can be read, as compared with a case where examination including tomosynthesis imaging is completed and then the tomographic images are transmitted to the external apparatus or a case where the tomographic images are transmitted to the external apparatus according to an instruction of the operator.

DETAILED DESCRIPTION

Figure 1:
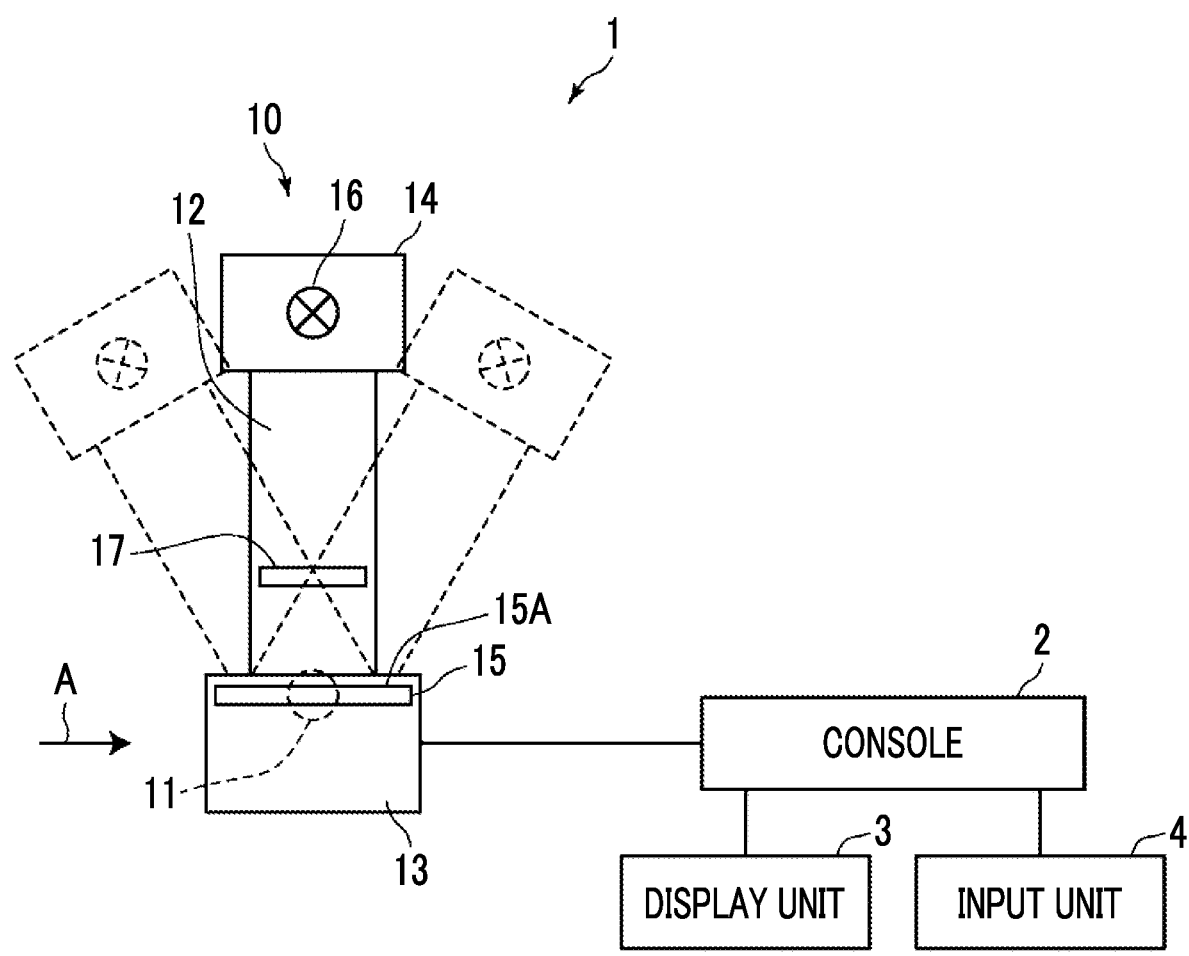
FIG. 1 is a schematic configuration diagram of a radiography system to which an image transmission apparatus according to an embodiment of the present disclosure is applied.
Figure 2:
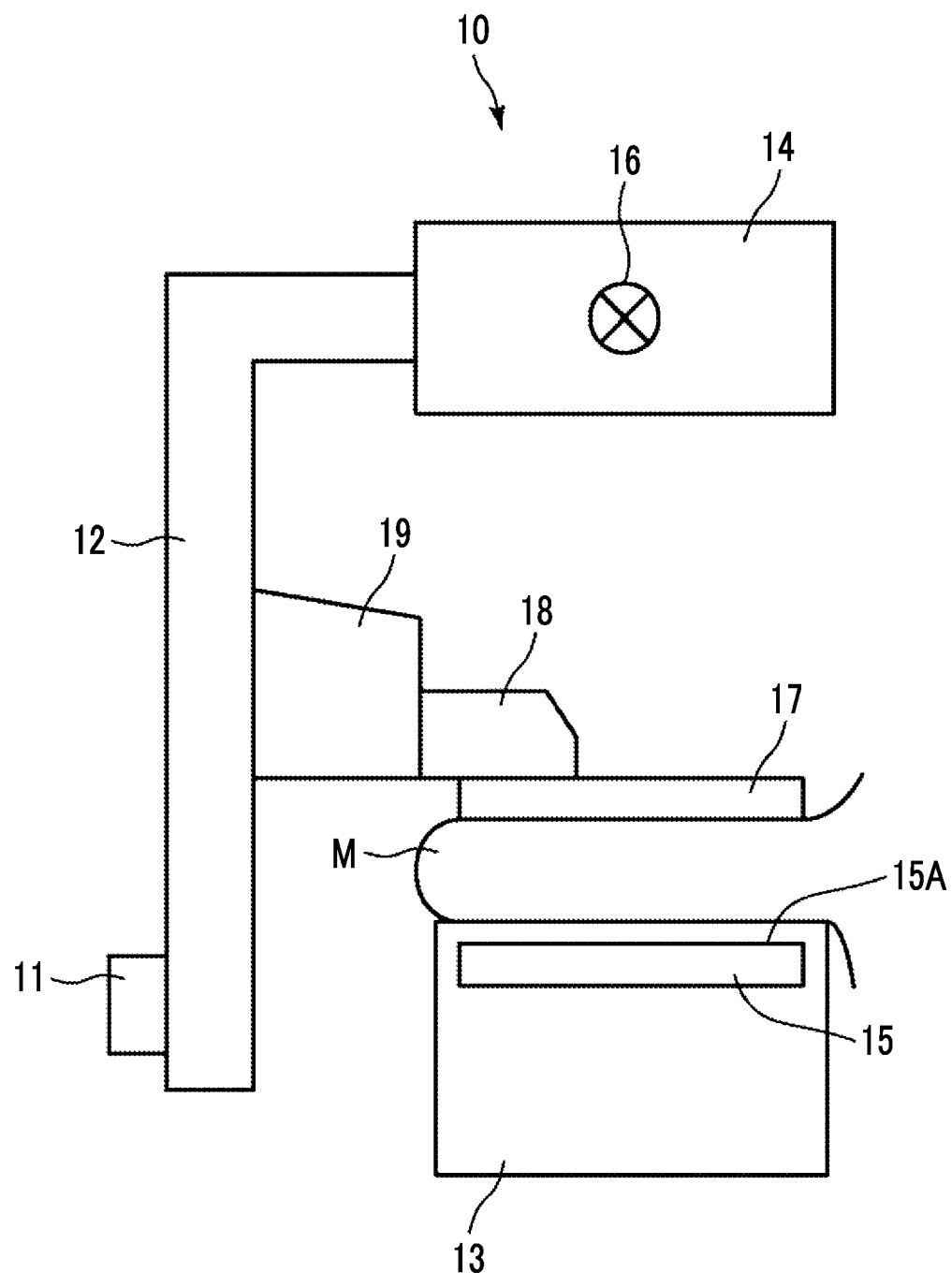
FIG. 2 is a diagram illustrating a mammography apparatus as viewed from a direction of an arrow A in FIG. 1.

Hereinafter, embodiments of the present disclosure will be described with reference to the drawings. FIG. 1 is a schematic configuration diagram of a radiography system to which an image transmission apparatus according to an embodiment of the present disclosure is applied, and FIG. 2 is a diagram illustrating a mammography apparatus included in the radiography system as viewed from a direction of an arrow A in FIG. 1.

As illustrated in FIG. 1, a radiography system 1 according to the present embodiment includes a console 2 and a mammography apparatus 10. The console 2 includes a display unit 3 and an input unit 4.

The radiography system 1 according to the present embodiment has a function of performing tomosynthesis imaging of a patient's breast by the mammography apparatus 10 and acquiring tomographic images of the breast on a plurality of tomographic planes, based on an imaging instruction (imaging order) for examination which is input from an external system (for example, a radiology information system (RIS)) via the console 2, in response to an operation of an operator such as a doctor or a radiologist. The tomosynthesis imaging is performed in a case where there is an imaging order for an examination including tomosynthesis imaging. In the present embodiment, the mammography apparatus 10 can generate a tomographic breast image and a two-dimensional breast image by performing both tomosynthesis imaging and simple imaging. The two-dimensional breast image means a breast image acquired by simple imaging.

The mammography apparatus 10 includes an arm portion 12 that is connected to a base (not illustrated) by a rotation shaft 11. An imaging table 13 is attached to one end of the arm portion 12, and a radiation irradiation unit 14 is attached to the other end of the arm portion 12 so as to face the imaging table 13. The arm portion 12 is configured such that only the end to which the radiation irradiation unit 14 is attached can be rotated. Therefore, the imaging table 13 is fixed and only the radiation irradiation unit 14 can be rotated. The rotation of the arm portion 12 is controlled by the console 2.

A radiation detector 15, such as a flat panel detector, is provided in the imaging table 13. The radiation detector 15 has a radiation detection surface 15A. In addition, a circuit board including a charge amplifier that converts a charge signal read from the radiation detector 15 into a voltage signal, a sampling two correlation pile circuit that samples the voltage signal output from the charge amplifier, and an analog-to-digital (AD) conversion unit that converts the voltage signal into a digital signal is provided in the imaging table 13. The radiation detector 15 corresponds to a detection unit. Further, in the present embodiment, as the detection unit, the radiation detector 15 is used. On the other hand, the detection unit is not limited to the radiation detector 15 as long as the detection unit can detect radiation and convert the radiation into an image.

The radiation detector 15 can repeatedly perform recording and reading of a radiographic image, may be a so-called direct-type radiation detector that directly converts radiation such as X-rays into charges, or may be a so-called indirect-type radiation detector that converts radiation such as X-rays into visible light once and converts the visible light into a charge signal. As a method for reading a radiographic image signal, it is desirable to use the following method: a so-called thin film transistor (TFT) reading method which reads a radiographic image signal by turning on and off a TFT switch; or a so-called optical reading method which reads a radiographic image signal by irradiating a target with read light. On the other hand, the reading method is not limited thereto, and other methods may be used.

A radiation source 16 is accommodated in the radiation irradiation unit 14. The radiation source 16 emits X-rays as radiation. The console 2 controls a timing when the radiation source 16 emits the radiation and radiation generation conditions of the radiation source 16, that is, selection of a target and filter materials, a tube voltage, an irradiation time, and the like.

Further, the arm portion 12 is provided with a compression plate 17 that is disposed above the imaging table 13 and presses and compresses the breast M, a support portion 18 that supports the compression plate 17, and a movement mechanism 19 that moves the support portion 18 in a vertical direction in FIG. 1 and FIG. 2. A distance between the compression plate 17 and the imaging table 13, that is, a compression thickness is input to the console 2.

The display unit 3 is a display device such as a cathode ray tube (CRT) or a liquid crystal monitor, and displays a projection image, a tomographic image, a composite two-dimensional image, which are acquired as described later, and messages required for operations. The display unit 3 may include a speaker that outputs sound.

The input unit 4 includes a keyboard, a mouse, and a touch-panel-type input device, and receives inputs to operate the mammography apparatus 10 from the operator. In addition, in a case where the examination is completed, an instruction indicating that the examination is completed is also received. Further, the input unit 4 receives an input of various kinds of information required for tomosynthesis imaging, such as imaging conditions, and an instruction to correct information. In the present embodiment, each unit of the mammography apparatus 10 is operated according to the information which is input from the input unit 4 by the operator.

In addition to an imaging program for performing tomosynthesis imaging, an image transmission program according to the present embodiment is installed in the console 2. In the present embodiment, the console 2 may be a workstation or a personal computer that is directly operated by the operator, or may be a server computer that is connected to the mammography apparatus 10 via a network. The image transmission program is distributed by being recorded on a recording medium such as a digital versatile disc (DVD) or a compact disc read only memory (CD-ROM), and is installed in a computer from the recording medium. Alternatively, the image transmission program is stored in a storage device of a server computer connected to the network or a network storage in a state where an access from the outside is allowed, and is downloaded and installed in the computer as required.

Figure 3:
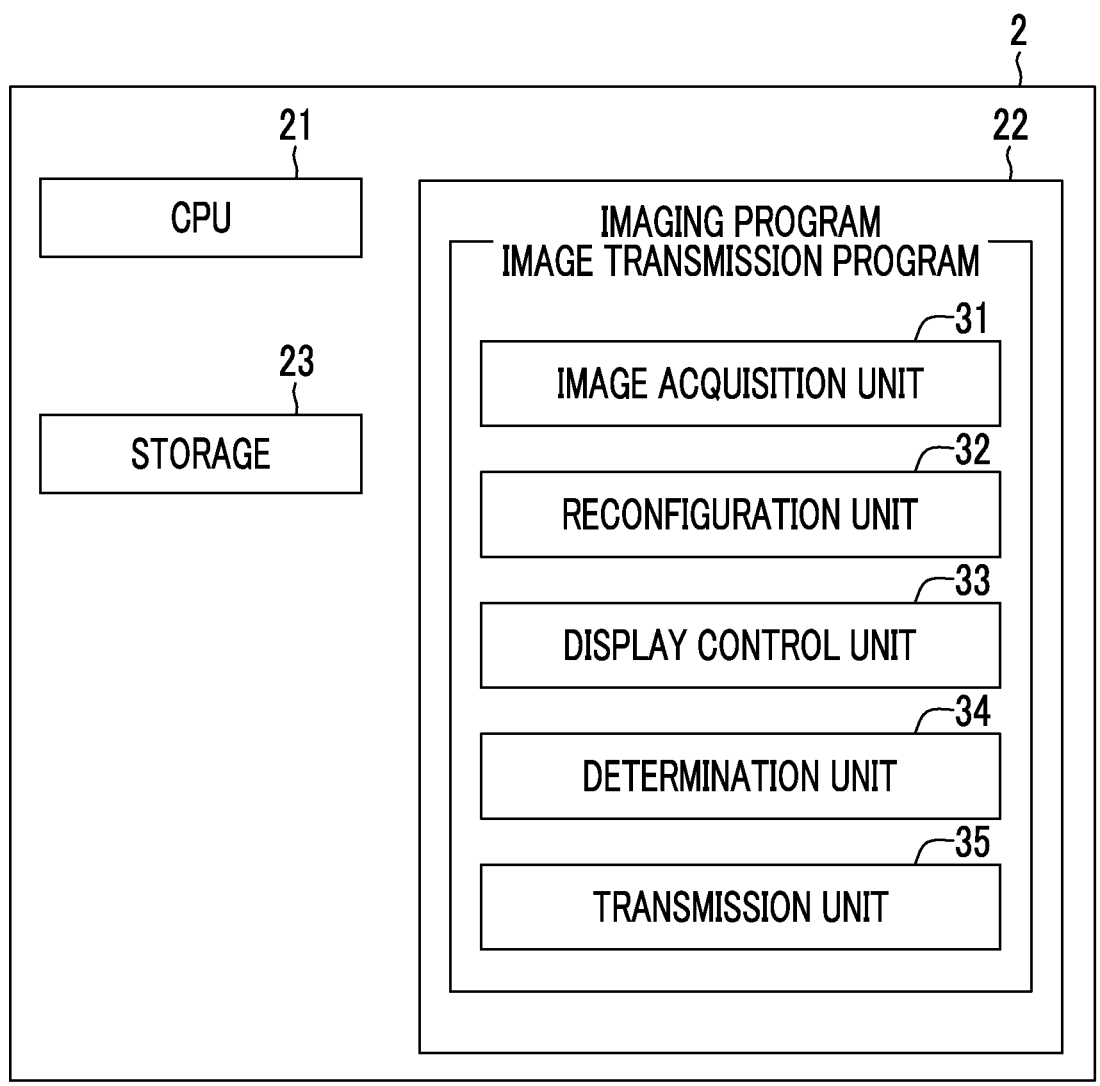
FIG. 3 is a diagram illustrating a schematic configuration of the image transmission apparatus realized by installing, in a computer as a console, an image transmission program according to the present embodiment.

FIG. 3 is a diagram illustrating a schematic configuration of the image transmission apparatus realized by installing, on the console 2, the image transmission program according to the present embodiment. As illustrated in FIG. 3, the image transmission apparatus includes, as a standard computer configuration, a central processing unit (CPU) 21, a memory 22, and a storage 23.

The storage 23 is a storage device such as a hard disk drive or a solid state drive (SSD), and stores various kinds of information including a tomosynthesis imaging program and the image transmission program for driving each unit of the mammography apparatus 10. Further, the storage 23 also stores the projection image acquired by tomosynthesis imaging and the tomographic image generated as described later.

The memory 22 temporarily stores the programs that are stored in the storage 23 in order to cause the CPU 21 to execute various processing. The imaging program and the image transmission program define the following processing as processing to be executed by the CPU 21: image acquisition processing of acquiring a plurality of projection images of the breast M corresponding to each of a plurality of radiation source positions by causing the mammography apparatus 10 to perform tomosynthesis imaging; reconfiguration processing of generating a plurality of tomographic images on each of a plurality of tomographic planes of the breast M as an object by reconfiguring the plurality of projection images; display control processing of sequentially displaying the tomographic images which are sequentially generated on the display unit; determination processing of determining whether or not at least one tomographic image is visually recognized by the operator; and transmission processing of transmitting the plurality of tomographic images to an external apparatus in a case where it is determined that at least one tomographic image is visually recognized by the operator.

The CPU 21 executes the processing according to the imaging program and the image transmission program, and thus the computer 2 functions as an image acquisition unit 31, a reconfiguration unit 32, a display control unit 33, a determination unit 34, and a transmission unit 35.

The image acquisition unit 31 acquires a plurality of projection images by causing the mammography apparatus 10 to perform tomosynthesis imaging according to the imaging program. That is, the image acquisition unit 31 acquires a plurality of projection images Gi (i=1 to n, where n is the number of radiation source positions and is, for example, 15) at a plurality of radiation source positions by moving the radiation source 16 by rotating the arm portion 12 around the rotation shaft 11, irradiating the breast M as an object with radiation at a plurality of radiation source positions obtained by the movement of the radiation source 16 according to predetermined imaging conditions for tomosynthesis imaging, and detecting the radiation passing through the breast M by the radiation detector 15.

Figure 4:
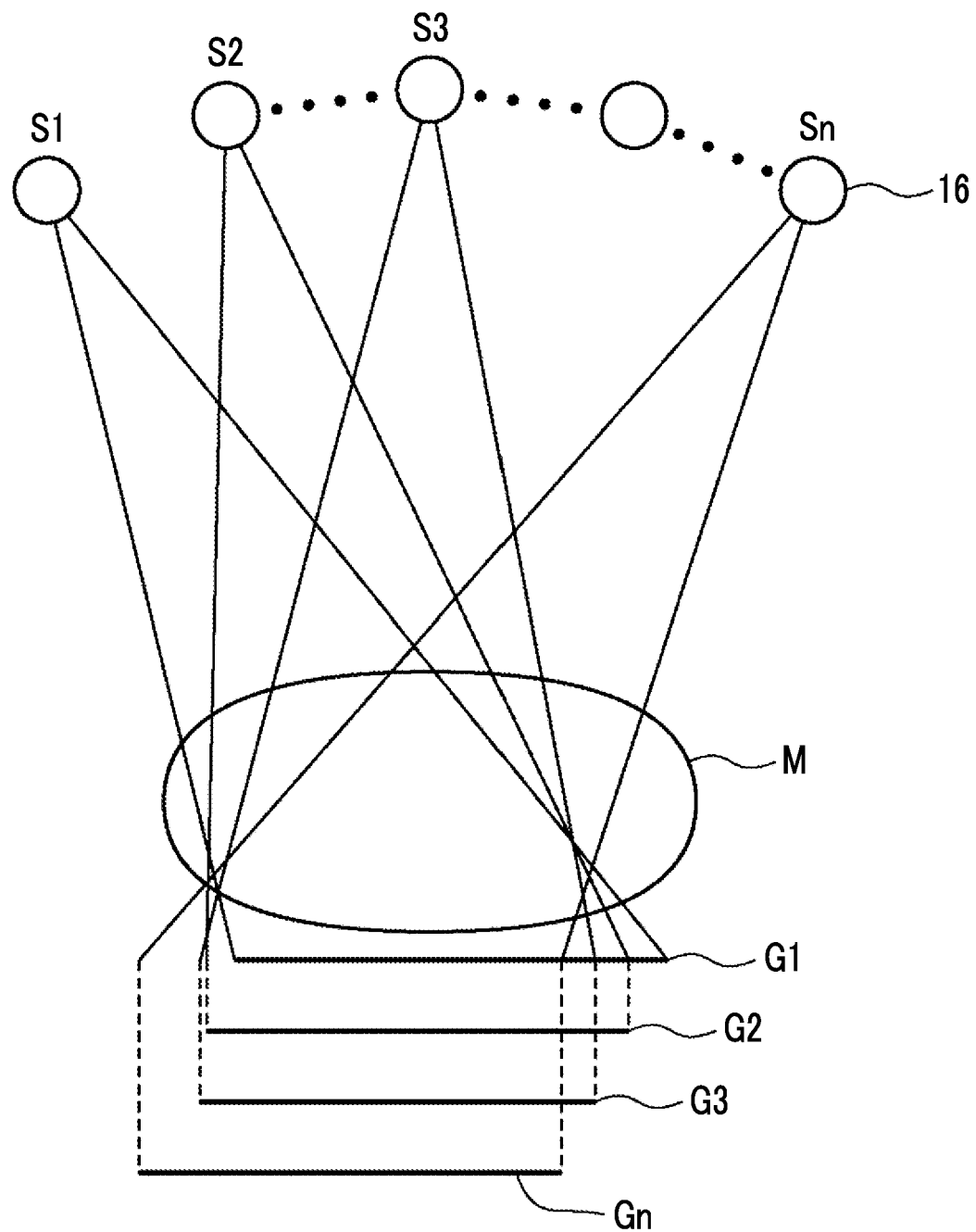
FIG. 4 is a diagram for explaining acquisition of projection images.

FIG. 4 is a diagram for explaining the acquisition of the projection images Gi. As illustrated in FIG. 4, the radiation source 16 is moved to each of radiation source positions S1, S2, S3, . . . , Sn. The radiation source 16 drives and irradiates the breast M with radiation at each of the radiation source positions. The radiation detector 15 detects X-rays passing through the breast M, and thus the projection images G1, G2, G3, . . . , Gn corresponding to the radiation source positions S1 to Sn are acquired. At each of the radiation source positions S1 to Sn, the breast M is irradiated with the same dose of radiation. The plurality of acquired projection images Gi are sequentially output to the display control unit 33, and sequentially stored in the storage 23.

Figure 5:
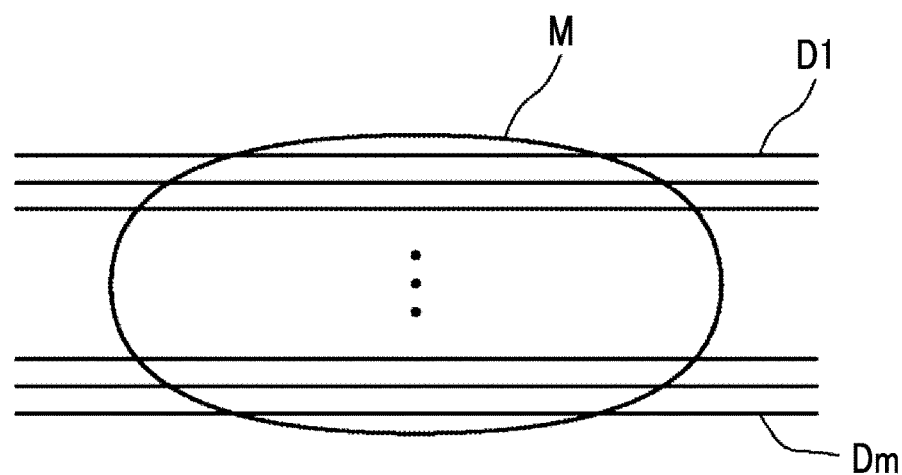
FIG. 5 is a diagram for explaining generation of tomographic images.

The reconfiguration unit 32 sequentially generates tomographic images in which the desired tomographic planes of the breast M are highlighted by reconfiguring the plurality of projection images Gi. Specifically, the reconfiguration unit 32 sequentially generates a plurality of tomographic images Dj (j=1 to m) on each of the plurality of tomographic planes of the breast M as illustrated in FIG. 5 by reconfiguring the plurality of projection images Gi using a known inverse projection method, such as a simple inverse projection method or a filtering inverse projection method. In this case, a three-dimensional coordinate position in a three-dimensional space including the breast M is set, pixel values at corresponding pixel positions in the plurality of projection images Gi are reconfigured with respect to the set three-dimensional coordinate position, and pixel values at the coordinate positions are calculated. The order of generation of the tomographic images Dj may be from the tomographic image D1 on the uppermost tomographic plane of the breast M, or may be from the tomographic image Dm on the lowermost tomographic plane of the breast M. The tomographic images sequentially generated by the reconfiguration unit 32 are sequentially output to the display control unit 33, and are sequentially stored in the storage 23.

Figure 6:
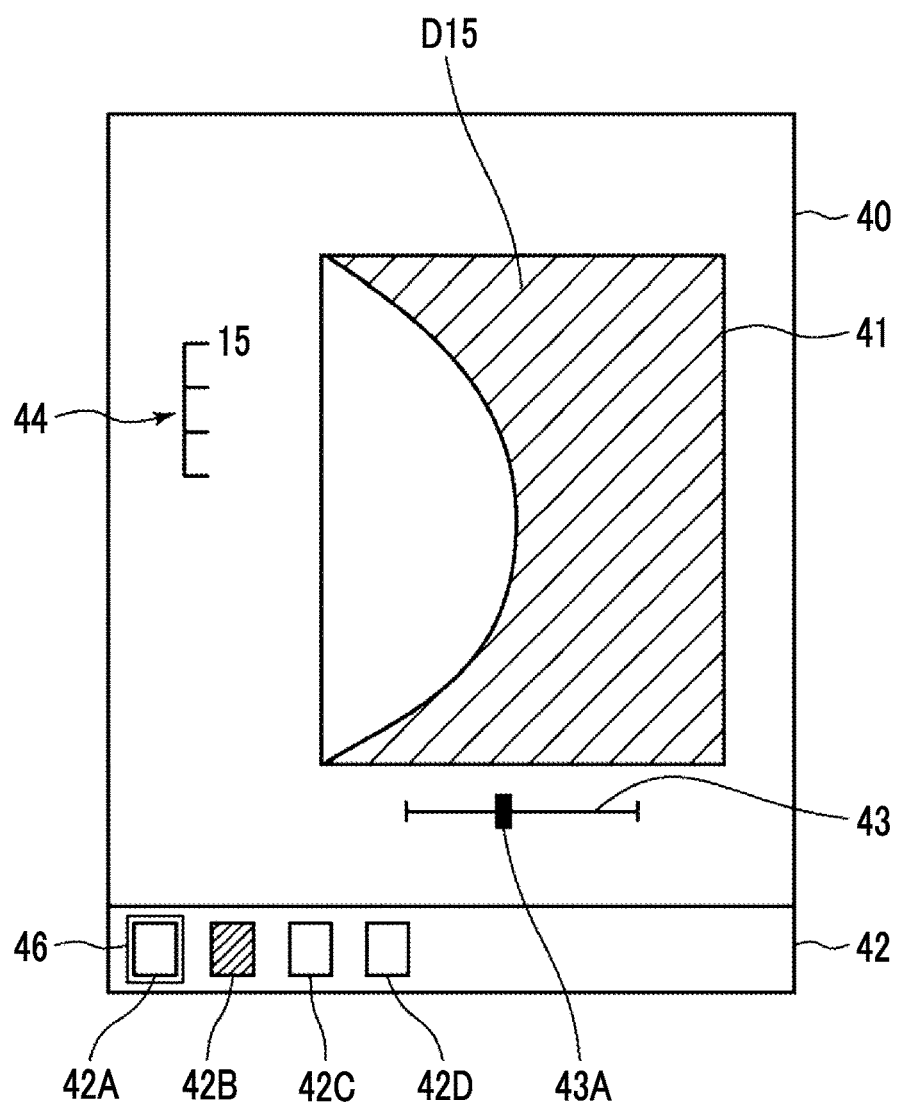
FIG. 6 is a diagram illustrating an image display screen.

The display control unit 33 displays the tomographic images Dj which are sequentially generated by the reconfiguration unit 32, on the display unit 3, in the order of generation. The display control unit 33 also displays the projection images Gi which are acquired by the image acquisition unit 31, on the display unit 3, in the order of acquisition. FIG. 6 is a diagram illustrating an image display screen displayed on the display unit 3. First, the display control unit 33 displays the projection images Gi, in an image display area 41 of the image display screen 40, in the order of acquisition. In a case where the acquisition of all the projection images Gi is completed and the reconfiguration unit 32 starts to generate the tomographic images Dj, the display control unit 33 sequentially displays the generated tomographic images Dj in the image display area 41.

The image display screen 40 includes an imaging menu display area 42. In the imaging menu display area 42, icons representing imaging menus for each imaging order are arranged and displayed. In FIG. 6, four icons 42A to 42D are displayed in a selectable state. In a case of the icon of the imaging menu in which imaging and generation of the tomographic images are currently being performed, a color is changed or a frame is added so as to be distinguishable from other imaging menus. FIG. 6 illustrates a state where a color of the second icon 42B from the left is changed by adding hatching. In addition, in a case of another icon of another imaging menu in which imaging is completed, a color is changed or a frame is added so as to be distinguishable from other imaging menus. In FIG. 6, the leftmost icon 42A is displayed by adding a frame 46 indicating that imaging is completed.

On the other hand, a slide bar 43 and a scale 44 are displayed on the image display screen 40. The slide bar 43 includes a control 43A. By changing a position of the control 43A of the slide bar 43, it is possible to instruct a height of the tomographic plane of the tomographic image to be displayed in the image display area 41. Specifically, in a case where the operator moves the control 43A to the left or right by inputting an instruction via the input unit 4, the display control unit 33 switches and displays the tomographic images Dj displayed in the image display area 41 according to the position of the control 43A. During the generation of the tomographic images Dj, the tomographic images Dj are displayed in the image display area 41 in the order of the generation. Thus, the control 43A continues to move from left to right until the generation of the tomographic images Dj is completed. Further, in the present embodiment, in a case where the input unit 4 includes a mouse, the tomographic images Dj to be displayed can be switched by operation of a wheel of the mouse.

Figure 7:
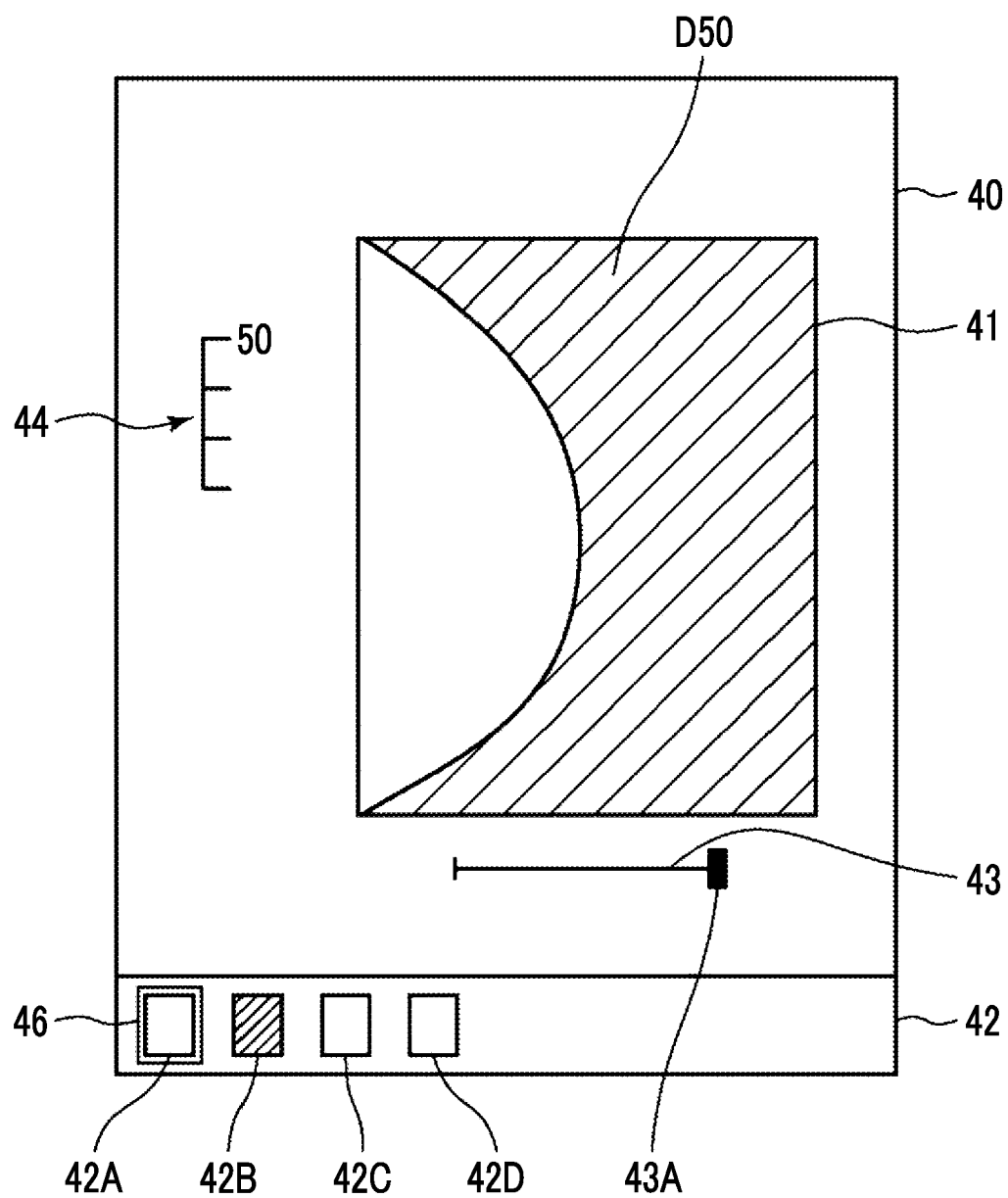
FIG. 7 is a diagram illustrating the image display screen on which the last tomographic image is displayed.

The scale 44 represents the number of the generated tomographic images Dj. In FIG. 6, a number of "15" is displayed. This indicates that the tomographic image Dj currently being displayed is the 15th tomographic image D15. During the generation of the tomographic images Dj, the number on the scale 44 is sequentially increased, and in a case where the generation of the tomographic images Dj is completed, the number of the generated tomographic images Dj is stopped. In the present embodiment, it is assumed that 50 tomographic images Dj are generated. Thus, in a case where the 50th tomographic image D50 is generated, the tomographic image D50 is displayed in the image display area 41 as illustrated in FIG. 7, and the control 43A of the slide bar 43 is moved to the rightmost end. Further, the number on the scale 44 stops at 50.

The determination unit 34 determines whether or not at least one tomographic image is visually recognized by the operator. In the present embodiment, the following first to seventh aspects can be used to determine whether or not at least one tomographic image is visually recognized by the operator.

In a first aspect, in a case where the generation of all the tomographic images Dj is completed and the display control unit 33 displays the last tomographic image on the display unit 3, the determination unit 34 determines that at least one tomographic image is visually recognized by the operator. Here, among the plurality of tomographic images Dj which are sequentially generated, the tomographic image which is generated last is referred to as the last tomographic image. In a case where the tomographic images are generated from the lower tomographic plane to the upper tomographic plane of the breast M, the last tomographic image is the tomographic image at the uppermost tomographic plane. On the other hand, in a case where the tomographic images are generated from the upper tomographic plane to the lower tomographic plane of the breast M, the last tomographic image is the tomographic image at the lowermost tomographic plane. In the first aspect, as illustrated in FIG. 7, in a case where the display control unit 33 displays the last tomographic image D50 in the image display area 41 of the image display screen 40, the determination unit 34 determines that at least one tomographic image is visually recognized by the operator.

In a second aspect, in a case where the generation of all the tomographic images Dj is completed and the display control unit 33 displays a predetermined number of the tomographic images on the tomographic planes which are different from the last tomographic image on the display unit 3 according to an instruction of the operator, the determination unit 34 determines that at least one tomographic image is visually recognized by the operator. Specifically, as illustrated in FIG. 7, in a case where the display control unit 33 displays the last tomographic image D50 in the image display area 41 of the image display screen 40 and then the display control unit 33 displays a predetermined number of the tomographic images on the tomographic planes which are different from the last tomographic image D50 in the image display area 41 according to an instruction of the operator, the determination unit 34 determines that at least one tomographic image is visually recognized by the operator. At this time, the operator switches the tomographic images displayed in the image display area 41 by operating the control 43A of the slide bar 43. Alternatively, in a case where the input unit 4 includes a mouse, the operator switches the tomographic images displayed in the image display area 41 by rotating a wheel of the mouse.

Here, in the present embodiment, it is assumed that the display control unit 33 assigns a flag to the displayed tomographic image. In the present embodiment, in a case where the tomographic images are generated, a database for the generated tomographic images is generated in the storage 23. After the last tomographic image is generated, the display control unit 33 assigns "1" to a flag of the database for the tomographic images which are displayed in the image display area 41 of the image display screen 40 according to an instruction of the operator. For the tomographic images which are not displayed, the flag is set to "0". In the second aspect, flags for all the tomographic images are monitored, and in a case where flags are assigned to a predetermined number of the tomographic images other than the last tomographic image, the determination unit 34 determines that at least one tomographic image is visually recognized by the operator.

Further, in the second aspect, the predetermined number may be set to an arbitrary number equal to or larger than 1. The predetermined number may be set by inputting a numerical value via the input unit 4, and may be set to the number of all the tomographic images, the number corresponding to 1/k1 (k1 is a natural number) of all the tomographic images, or the number corresponding to 1/k2 (k2 is a natural number) of the compression thickness of the breast M. Here, the number of the tomographic images to be displayed may be determined by the number of flags assigned to the tomographic images.

In the present embodiment, in a case where the control 43A is operated or the wheel of the mouse is operated until the desired tomographic image on the tomographic plane is displayed from the displayed tomographic image (for example, the last tomographic image), the tomographic images existing between the two tomographic images are switched and sequentially displayed in the image display area 41. On the other hand, the display of the tomographic images is instantaneous, and is clearly shorter than a display time which allows the operator to visually recognize the desired tomographic image on the tomographic plane. For this reason, in the present embodiment, "displaying a tomographic image" means displaying a tomographic image for a predetermined time, for example, a time equal to or longer than 0.5 seconds. That is, in the present embodiment, in a case where the tomographic image is displayed for a predetermined time or longer, the flag "1" is assigned to the tomographic image.

Figure 8:
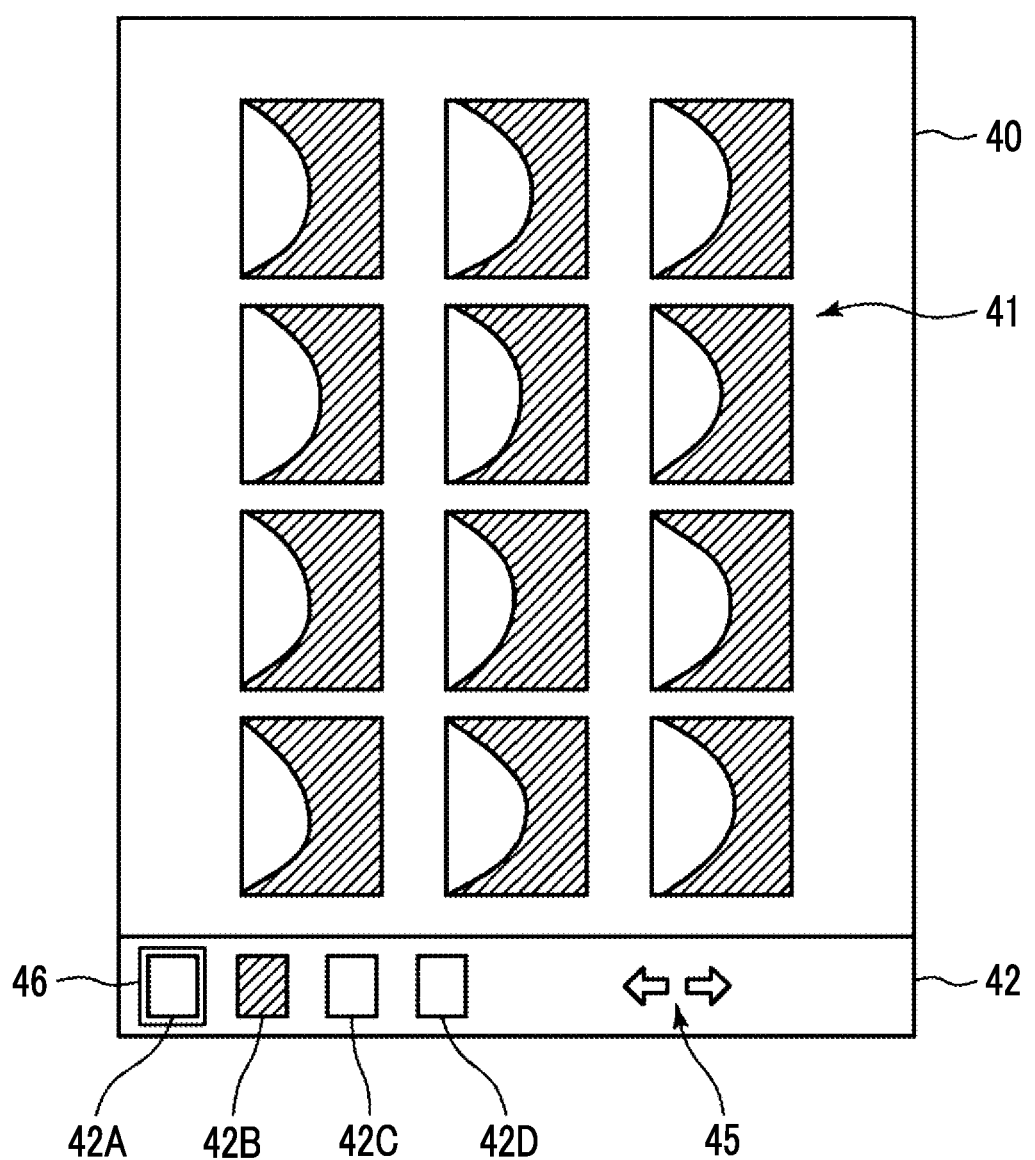
FIG. 8 is a diagram illustrating the image display screen on which a plurality of tomographic images are displayed at the same time.

In a third aspect, in a case where the generation of all the tomographic images Dj is completed and the display control unit 33 displays two or more tomographic images among the plurality of tomographic images on the display unit 3 at the same time according to an instruction of the operator, the determination unit 34 determines that at least one tomographic image is visually recognized by the operator. Displaying two or more tomographic images on the display unit 3 at the same time means displaying two or more tomographic images (12 images in this case) in the image display area 41 of the image display screen 40 at the same time as illustrated in FIG. 8. In the imaging menu display area 42 of the image display screen 40 illustrated in FIG. 8, left and right arrows 45 are displayed. In a case where the operator selects the right arrow using the input unit 4, the next 12 tomographic images are displayed in the image display area 41, and in a case where the operator selects the left arrow, the previous 12 tomographic images are displayed in the image display area 41. In this case, the display control unit 33 assigns a flag to all the tomographic images displayed on the display unit 3.

In a fourth aspect, after the generation of all the tomographic images Dj is completed, in a case where the display control unit 33 displays a predetermined number of the tomographic images on the tomographic planes, which are different from the tomographic plane of the last tomographic image, on the display unit 3 according to an instruction of the operator and a certain time has passed after the display, the determination unit 34 determines that at least one tomographic image is visually recognized by the operator.

In a fifth aspect, after the generation of all the tomographic images Dj is completed, in a case where the display control unit 33 displays two or more tomographic images among the plurality of tomographic images on the display unit 3 at the same time according to an instruction of the operator and a certain time has passed after the display, the determination unit 34 determines that at least one tomographic image is visually recognized by the operator.

In the fourth aspect and the fifth aspect, the certain time may be, for example, a time of two seconds to three seconds. The certain time may be set in advance by an input from the input unit 4. In the case of the fourth aspect, a starting point of the certain time may be a time when the operator stops an operation of switching the tomographic images to be displayed. Further, in the case of the fifth aspect, a starting point of the certain time may be a time when the display of two or more tomographic images at the same time is completed.

In a sixth aspect, after the generation of all the tomographic images Dj is completed, in a case where the display control unit 33 displays a predetermined number of the tomographic images on the tomographic planes, which are different from the tomographic plane of the last tomographic image, on the display unit 3 according to an instruction of the operator and a predetermined operation is further received, the determination unit 34 determines that at least one tomographic image is visually recognized by the operator.

In a seventh aspect, after the generation of all the tomographic images Dj is completed, in a case where the display control unit 33 displays two or more tomographic images among the plurality of tomographic images on the display unit 3 at the same time according to an instruction of the operator and a predetermined operation is further received, the determination unit 34 determines that at least one tomographic image is visually recognized by the operator.

In the sixth aspect and the seventh aspect, the predetermined operation includes an operation for moving to the next imaging, an operation for instructing display of different images obtained by imaging, and the like.

The operation for moving to the next imaging includes an operation of selecting, among a plurality of icons displayed in the imaging menu display area 42, an icon of the next imaging menu that is next to the imaging menu in which the tomographic image is currently displayed. For example, as illustrated in FIG. 7, the operation for moving to the next imaging includes an operation of selecting, among the plurality of icons 42A to 42D displayed in the imaging menu display area 42, the icon 42C of the next imaging menu that is on a right side of the icon 42B of the imaging menu in which the tomographic image is currently displayed. In this case, imaging according to the imaging menu corresponding to the selected icon 42C is performed.

The operation of instructing display of different images obtained by imaging includes an operation of selecting, among the plurality of icons displayed in the imaging menu display area 42, an icon of the imaging menu in which imaging is completed. For example, as illustrated in FIG. 7, the operation of instructing display of different images obtained by imaging includes an operation of selecting, among the plurality of icons 42A to 42D displayed in the imaging menu display area 42, the icon 42A of the imaging menu in which imaging is completed, the icon 42A being on a left side of the icon 42B of the imaging menu in which the tomographic image is currently displayed. In this case, the tomographic image acquired by the imaging menu corresponding to the selected icon 42A is displayed in the image display area 41.

The transmission unit 35 includes an interface connected to an external apparatus via a network. In a case where the determination unit 34 determines that at least one tomographic image is visually recognized by the operator, the transmission unit 35 transmits the plurality of tomographic images to the external apparatus such as an image storage server or an image viewer. Specifically, in a case where the examination including tomosynthesis imaging according to the current imaging menu is completed, before the operator instructs completion of the examination via the input unit 4 or before the operator instructs transmission of the plurality of tomographic images to the external apparatus via the input unit 4, the transmission unit 35 transmits the plurality of tomographic images to the external apparatus. Thereby, in the present embodiment, before the input unit 4 receives, from the operator, an instruction of completion of the examination including tomosynthesis imaging or before the input unit 4 receives, from the operator, an instruction of transmission of the plurality of tomographic images to the external apparatus, the plurality of tomographic images are transmitted to the external apparatus. Therefore, in a case where the operator instructs completion of the examination including tomosynthesis imaging or in a case where the operator instructs transmission of the plurality of tomographic images to the external apparatus, transmission of all the tomographic images to the external apparatus is completed or the plurality of tomographic images are being transmitted to the external apparatus.

Depending on the imaging menu, a combination of tomosynthesis imaging and simple imaging with the same positioning as the tomosynthesis imaging may be designated. The same positioning means that, in a case where a subject is a breast, tomosynthesis imaging and simple imaging are performed under the same compression condition. In this case, imaging is performed in order of tomosynthesis imaging and simple imaging. Even in this case, the determination by the determination unit 34 is performed in association with the display of the tomographic images acquired by the tomosynthesis imaging. Thus, in the present embodiment, before the operator instructs completion of the examination including tomosynthesis imaging or before the operator instructs transmission of the plurality of tomographic images to the external apparatus, the transmission unit 35 transmits the tomographic images to the external apparatus. Further, since the simple imaging is performed after tomosynthesis imaging, the simple two-dimensional image acquired by simple imaging is visually recognized after the tomographic image acquired by tomosynthesis imaging is displayed. Therefore, before the operator instructs completion of the examination including simple imaging, the transmission unit 35 transmits the tomographic images to the external apparatus.

Figure 9:
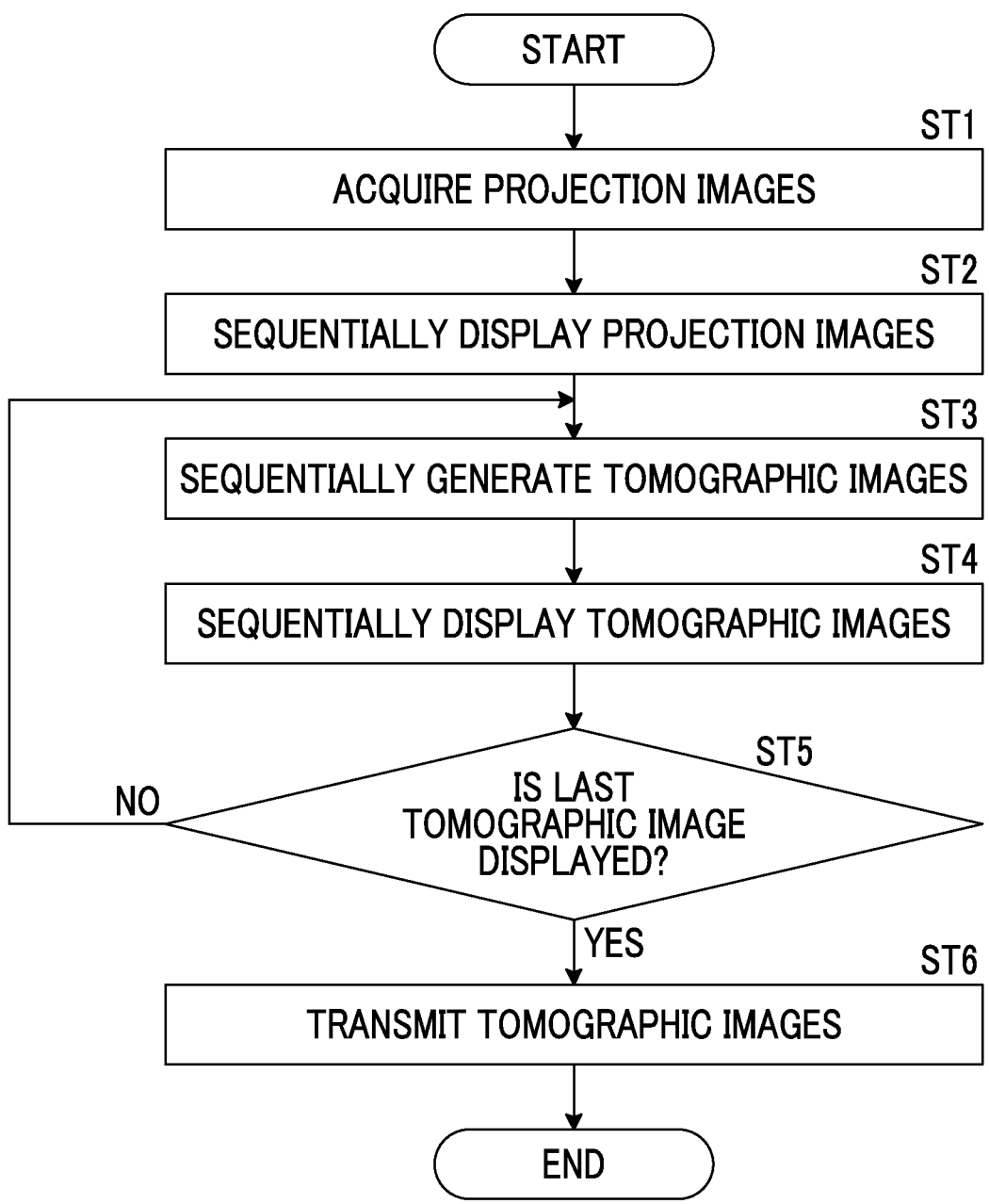
FIG. 9 is a flowchart illustrating processing in a case where determination according to a first aspect of the present embodiment is performed.

Next, processing performed in the present embodiment will be described. First, processing in a case where the determination according to the first aspect is performed will be described. FIG. 9 is a flowchart illustrating processing in a case where the determination according to the first aspect of the present embodiment is performed. In a case where the input unit 4 receives an instruction to start processing by the operator, tomosynthesis imaging is performed, and the image acquisition unit 31 acquires a plurality of projection images Gi (step ST1). The display control unit 33 sequentially displays the acquired projection images Gi on the display unit 3 (step ST2). Next, the reconfiguration unit 32 sequentially generates a plurality of tomographic images Dj on a plurality of tomographic planes of the breast M by reconfiguring the plurality of projection images Gi (step ST3). The display control unit 33 sequentially displays the generated tomographic images Dj on the display unit 3 (step ST4).

The determination unit 34 determines whether or not the display control unit 33 displays the last tomographic image on the display unit 3 (step ST5). In a case where a determination result in step ST5 is NO, the process returns to step ST3, and then processing of step ST3 and subsequent steps is repeated. In a case where a determination result in step ST5 is YES, the transmission unit 35 transmits the plurality of generated tomographic images Dj to the external apparatus (step ST6), and processing is ended.

Thereby, in the first aspect, images having large amounts of data such as the plurality of tomographic images can be transmitted to the external apparatus without waiting for the operator to instruct completion of the examination including tomosynthesis imaging or the operator to instruct transmission of the plurality of tomographic images to the external apparatus. Therefore, at a timing when the operator instructs completion of the examination or at a timing when the operator instructs transmission of the plurality of tomographic images to the external apparatus, the transmission of the plurality of tomographic images is completed or the transmission of the plurality of tomographic images is already started. Therefore, according to the first aspect of the present embodiment, in a case where it is desired to display and read the tomographic images stored in the external apparatus, it is possible to reduce a waiting time from a time when imaging is completed to a time when the tomographic images can be read, as compared with a case where tomosynthesis imaging is completed and then the tomographic images are transmitted to the external apparatus or a case where the tomographic images are transmitted to the external apparatus according to an instruction of the operator.

Figure 10:
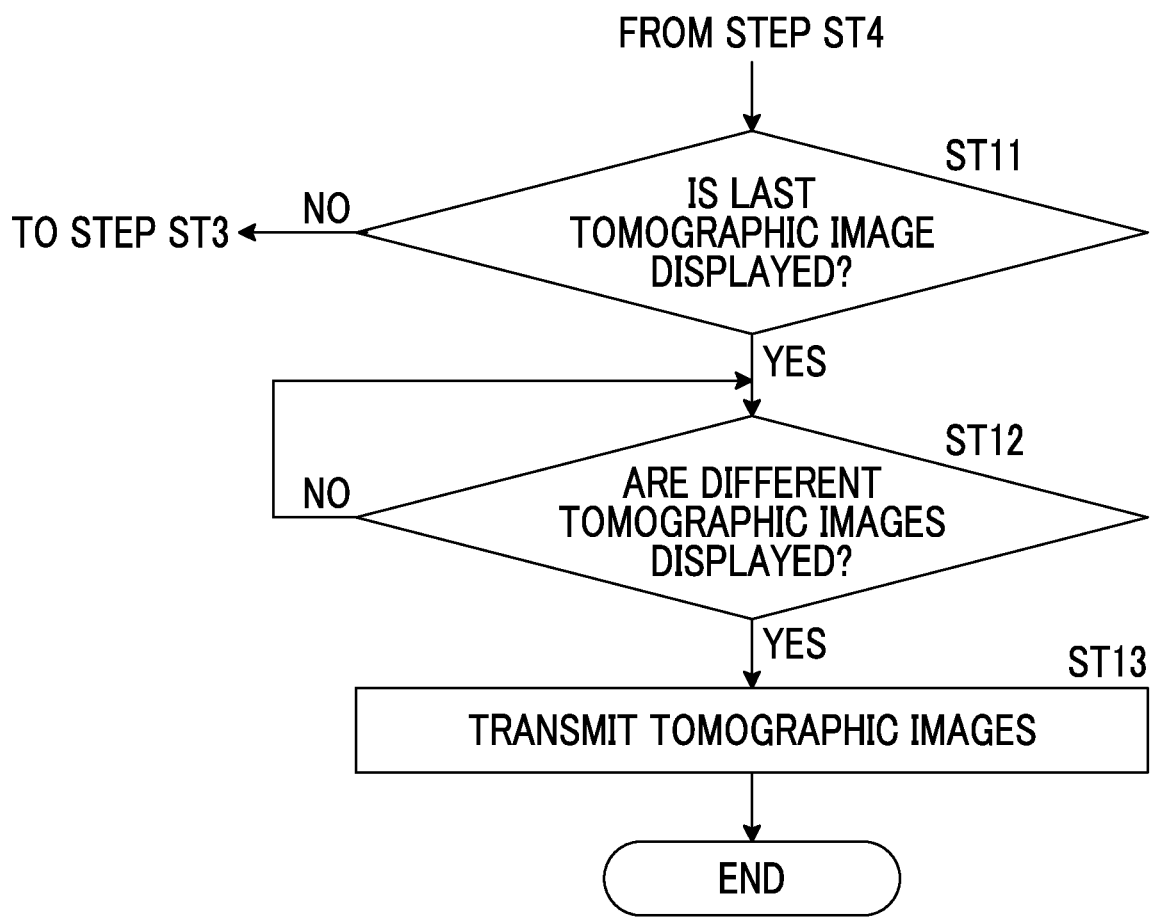
FIG. 10 is a flowchart illustrating processing in a case where determination according to a second aspect of the present embodiment is performed.

Next, processing in a case where the determination according to the second aspect is performed will be described. FIG. 10 is a flowchart illustrating processing in a case where the determination according to the second aspect of the present embodiment is performed. In the second aspect and the third to seventh aspects to be described below, processing until the tomographic images are sequentially displayed is the same as the processing in the first aspect. Thus, in FIG. 10 and FIGS. 11 to 15 to be described below, only the processing after step ST4 in the first aspect will be described. Following step ST4, the determination unit 34 determines whether or not the display control unit 33 displays the last tomographic image on the display unit 3 (step ST11). In a case where a determination result in step ST11 is NO, the process returns to step ST3, and then processing of step ST3 and subsequent steps is repeated.

In a case where a determination result in step ST11 is YES, the determination unit 34 further determines whether or not the display control unit 33 displays a predetermined number of the tomographic images on the tomographic planes that are different from the last tomographic image on the display unit 3 according to an instruction of the operator (whether or not the display control unit 33 displays different tomographic images, step ST12). In a case where a determination result in step ST12 is NO, processing of step ST12 is repeated. In a case where a determination result in step ST12 is YES, the transmission unit 35 transmits the plurality of generated tomographic images Dj to the external apparatus (step ST13), and processing is ended.

Thereby, in the second aspect, as in the first aspect, it is possible to reduce a waiting time from a time when imaging is completed to a time when the tomographic images can be read. Further, it is possible to more reliably perform determination as to whether the tomographic image is visually recognized by the operator, as compared with the determination in the first aspect.

Figure 11:
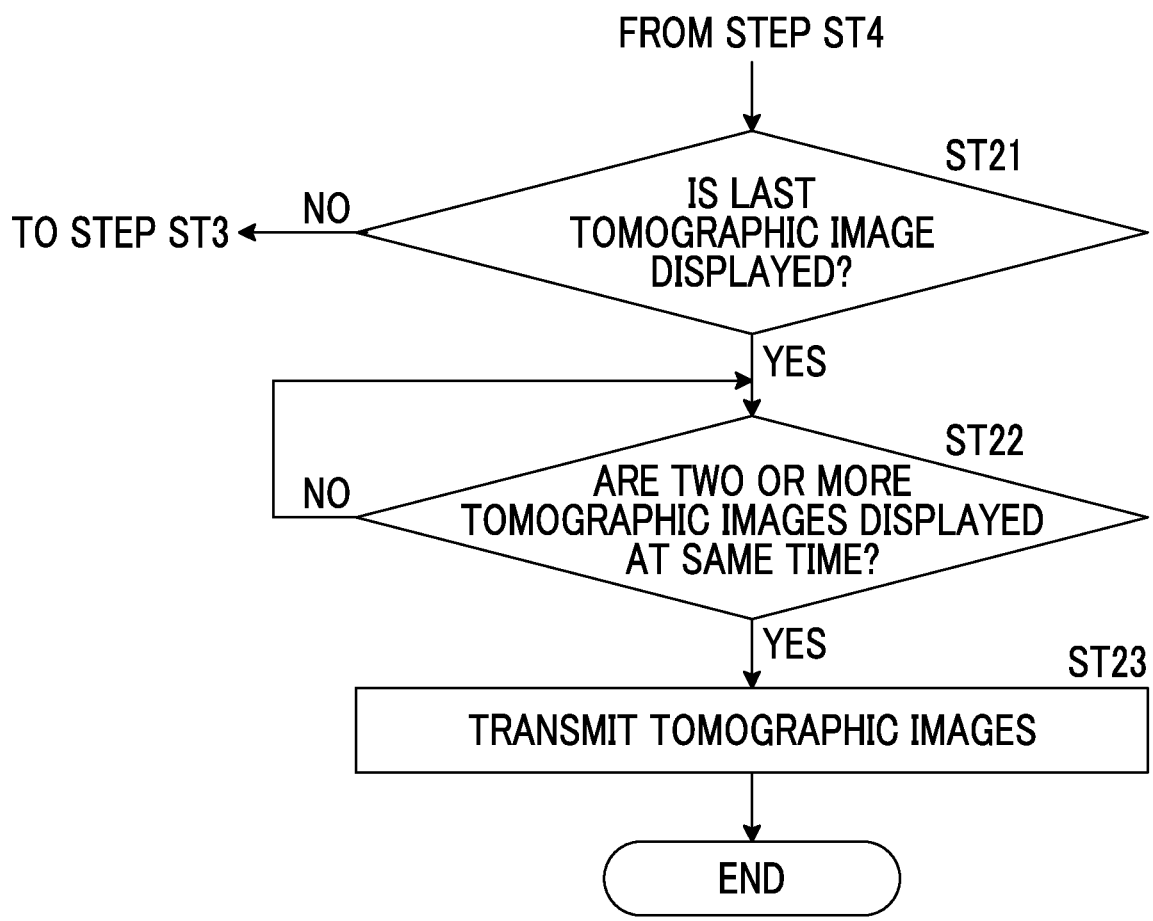
FIG. 11 is a flowchart illustrating processing in a case where determination according to a third aspect of the present embodiment is performed.

Next, processing in a case where the determination according to the third aspect is performed will be described. FIG. 11 is a flowchart illustrating processing in a case where the determination according to the third aspect of the present embodiment is performed. Following step ST4, the determination unit 34 determines whether or not the display control unit 33 displays the last tomographic image on the display unit 3 (step ST21). In a case where a determination result in step ST21 is NO, the process returns to step ST3, and then processing of step ST3 and subsequent steps is repeated.

In a case where a determination result in step ST21 is YES, the determination unit 34 further determines whether or not the display control unit 33 displays two or more tomographic images among the plurality of tomographic images on the display unit 3 at the same time according to an instruction of the operator (whether or not the display control unit 33 displays two or more tomographic images at the same time, step ST22). In a case where a determination result in step ST22 is NO, processing of step ST22 is repeated. In a case where a determination result in step ST22 is YES, the transmission unit 35 transmits the plurality of generated tomographic images Dj to the external apparatus (step ST23), and processing is ended.

Thereby, in the third aspect, as in the first aspect, it is possible to reduce a waiting time from a time when imaging is completed to a time when the tomographic images can be read. Further, it is possible to more reliably perform determination as to whether the tomographic image is visually recognized by the operator, as compared with the determination in the first aspect.

Figure 12:
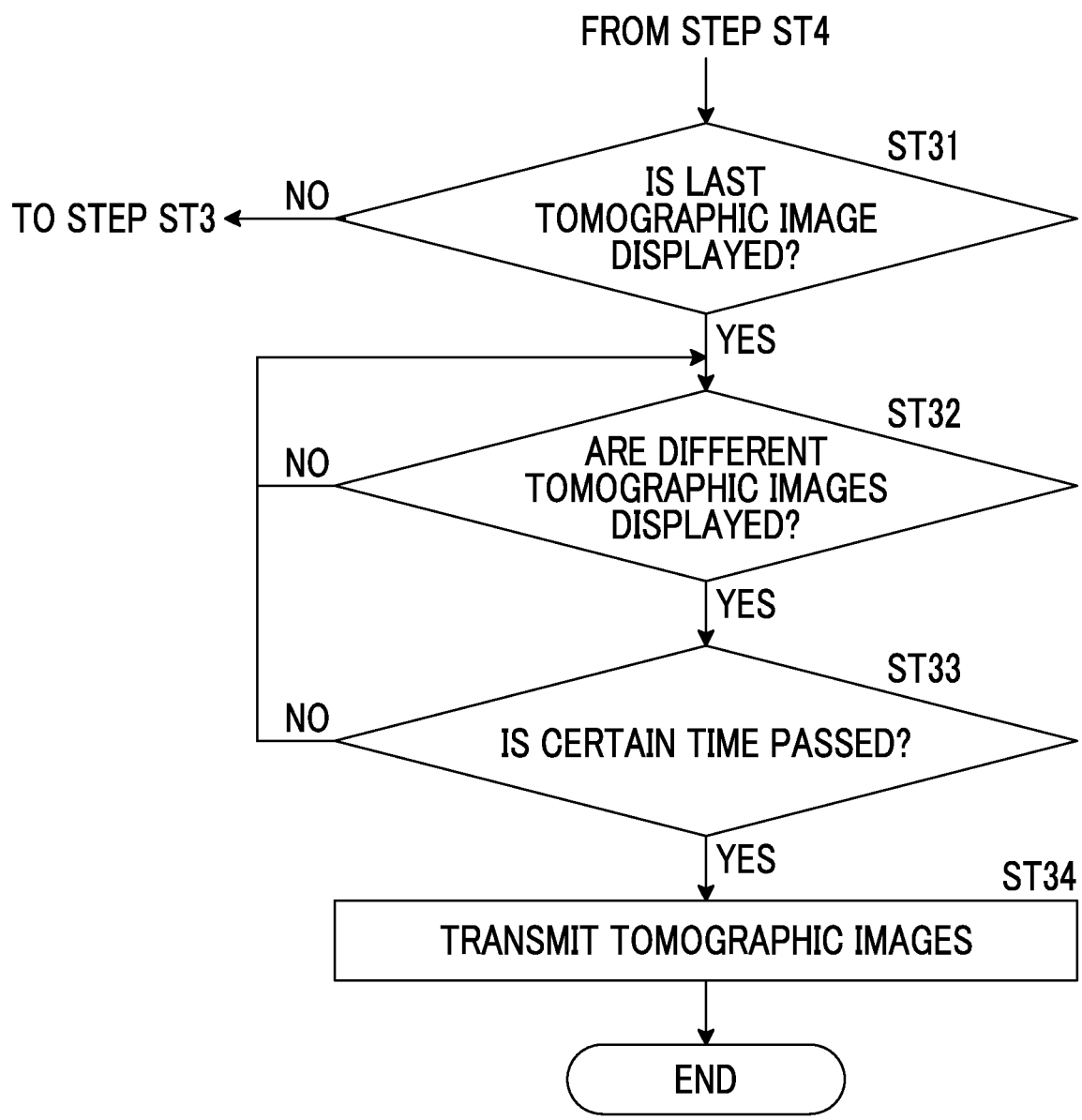
FIG. 12 is a flowchart illustrating processing in a case where determination according to a fourth aspect of the present embodiment is performed.

Next, processing in a case where the determination according to the fourth aspect is performed will be described. FIG. 12 is a flowchart illustrating processing in a case where the determination according to the fourth aspect of the present embodiment is performed. Following step ST4, the determination unit 34 determines whether or not the display control unit 33 displays the last tomographic image on the display unit 3 (step ST31). In a case where a determination result in step ST31 is NO, the process returns to step ST3, and then processing of step ST3 and subsequent steps is repeated.

In a case where a determination result in step ST31 is YES, the determination unit 34 further determines whether or not the display control unit 33 displays a predetermined number of the tomographic images on the tomographic planes that are different from the last tomographic image on the display unit 3 according to an instruction of the operator (whether or not the display control unit 33 displays different tomographic images, step ST32). In a case where a determination result in step ST32 is NO, processing of step ST32 is repeated. In a case where a determination result in step ST32 is YES, the determination unit 34 determines whether or not a certain time has passed after the display of the tomographic images (step ST33). In a case where a determination result in step ST33 is NO, the process returns to step ST32. In a case where a determination result in step ST33 is YES, the transmission unit 35 transmits the plurality of generated tomographic images Dj to the external apparatus (step ST34), and processing is ended.

Thereby, in the fourth aspect, as in the first aspect, it is possible to reduce a waiting time from a time when imaging is completed to a time when the tomographic images can be read. Further, in a case where the tomographic images are only switched and displayed, the tomographic images may be being recognized by the operator. On the other hand, in a case where a certain time has passed after the tomographic images are displayed, in many cases, recognition of the tomographic images is completed. In the fourth aspect, in a case where a certain time has passed after the tomographic images are displayed, the tomographic images are transmitted to the external apparatus. Therefore, it is possible to more reliably perform determination as to whether the tomographic image is visually recognized by the operator, as compared with the determination in the first aspect.

Figure 13:
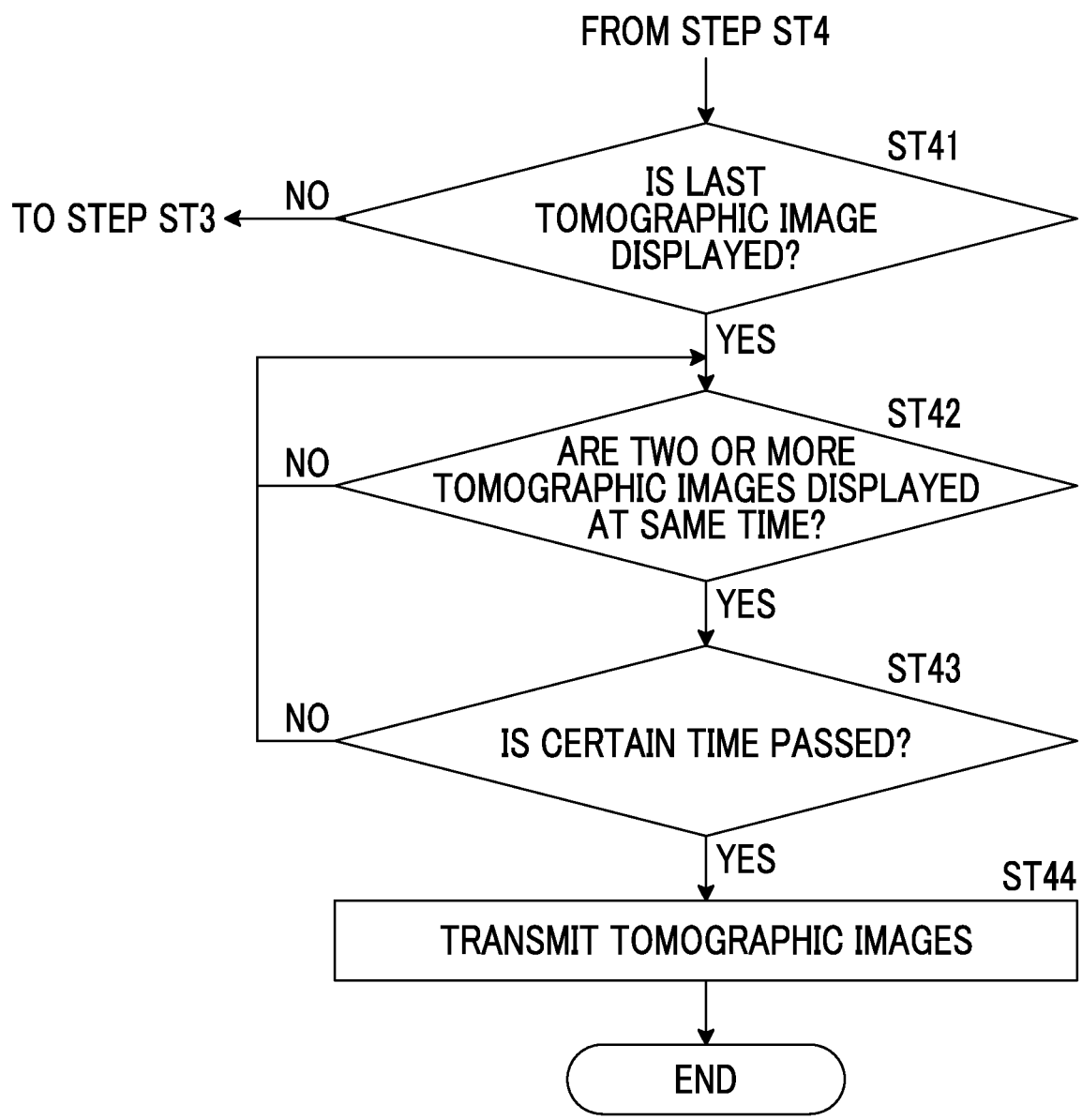
FIG. 13 is a flowchart illustrating processing in a case where the determination according to a fifth aspect of the present embodiment is performed.

Next, processing in a case where the determination according to the fifth aspect is performed will be described. FIG. 13 is a flowchart illustrating processing in a case where the determination according to the fifth aspect of the present embodiment is performed. Following step ST4, the determination unit 34 determines whether or not the display control unit 33 displays the last tomographic image on the display unit 3 (step ST41). In a case where a determination result in step ST41 is NO, the process returns to step ST3, and then processing of step ST3 and subsequent steps is repeated.

In a case where a determination result in step ST41 is YES, the determination unit 34 further determines whether or not the display control unit 33 displays two or more tomographic images among the plurality of tomographic images on the display unit 3 at the same time according to an instruction of the operator (whether or not the display control unit 33 displays two or more tomographic images at the same time, step ST42). In a case where a determination result in step ST42 is NO, processing of step ST42 is repeated. In a case where a determination result in step ST42 is YES, the determination unit 34 determines whether or not a certain time has passed after the display of the tomographic images (step ST43). In a case where a determination result in step ST43 is NO, the process returns to step ST42. In a case where a determination result in step ST43 is YES, the transmission unit 35 transmits the plurality of generated tomographic images Dj to the external apparatus (step ST44), and processing is ended.

Thereby, in the fifth aspect, as in the first aspect, it is possible to reduce a waiting time from a time when imaging is completed to a time when the tomographic images can be read. Further, in a case where the plurality of tomographic images are only displayed at the same time, the tomographic images may be being recognized by the operator. On the other hand, in a case where a certain time has passed after the tomographic images are displayed, in many cases, recognition of the tomographic images is completed. In the fifth aspect, in a case where a certain time has passed after the plurality of tomographic images are displayed at the same time, the tomographic images are transmitted to the external apparatus. Therefore, it is possible to more reliably perform determination as to whether the tomographic image is visually recognized by the operator, as compared with the determination in the first aspect.

Figure 14:
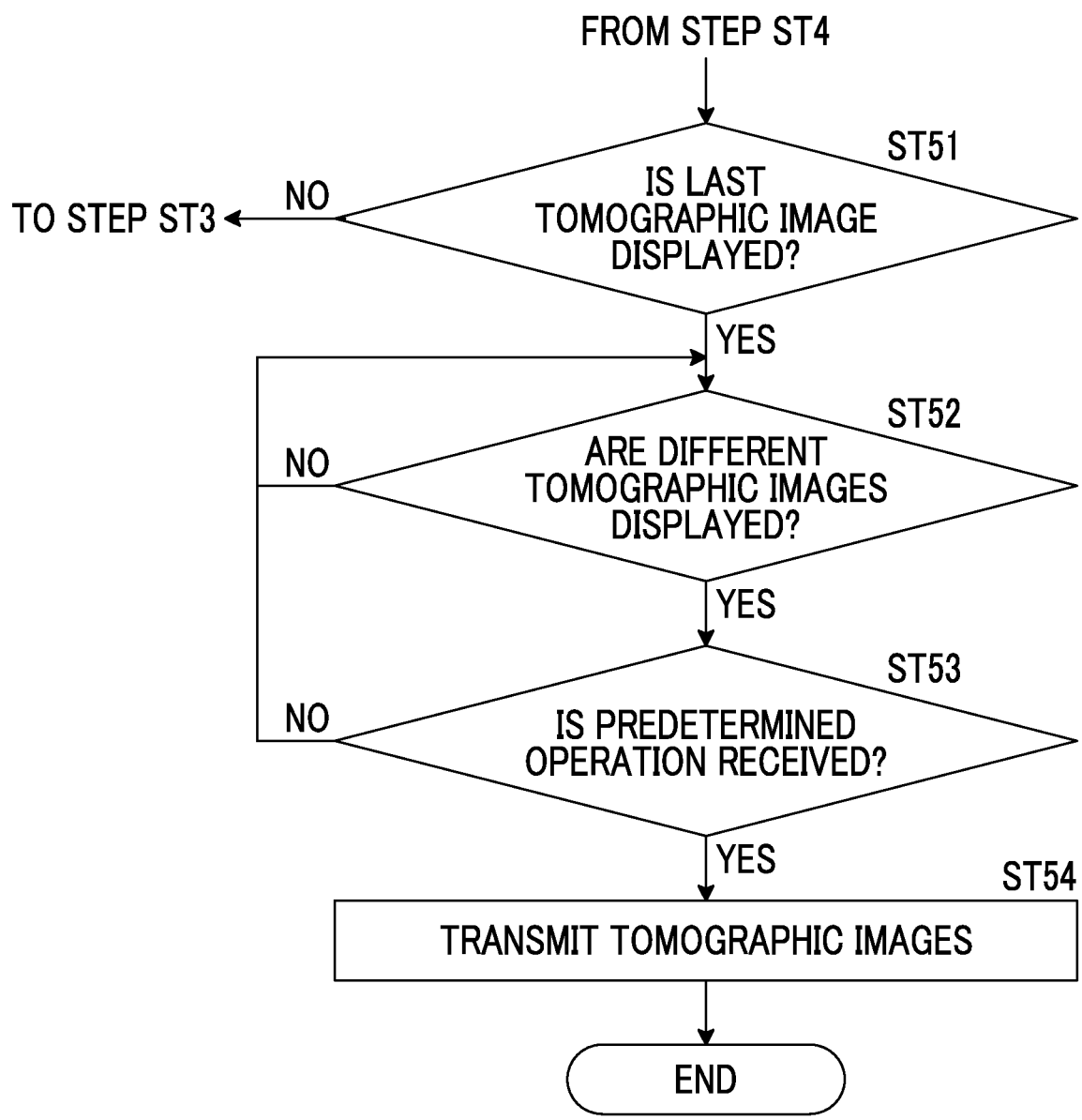
FIG. 14 is a flowchart illustrating processing in a case where determination according to a sixth aspect of the present embodiment is performed.

Next, processing in a case where the determination according to the sixth aspect is performed will be described. FIG. 14 is a flowchart illustrating processing in a case where the determination according to the sixth aspect of the present embodiment is performed. Following step ST4, the determination unit 34 determines whether or not the display control unit 33 displays the last tomographic image on the display unit 3 (step ST51). In a case where a determination result in step ST51 is NO, the process returns to step ST3, and then processing of step ST3 and subsequent steps is repeated.

In a case where a determination result in step ST51 is YES, the determination unit 34 further determines whether or not the display control unit 33 displays a predetermined number of the tomographic images on the tomographic planes that are different from the last tomographic image on the display unit 3 according to an instruction of the operator (whether or not the display control unit 33 displays different tomographic images, step ST52). In a case where a determination result in step ST52 is NO, processing of step ST52 is repeated. In a case where a determination result in step ST52 is YES, the determination unit 34 determines whether or not a predetermined operation is received (step ST53). In a case where a determination result in step ST53 is NO, the process returns to step ST52. In a case where a determination result in step ST53 is YES, the transmission unit 35 transmits the plurality of generated tomographic images Dj to the external apparatus (step ST54), and processing is ended.

Thereby, in the sixth aspect, as in the first aspect, it is possible to reduce a waiting time from a time when imaging is completed to a time when the tomographic images can be read. Further, in a case where the tomographic images are only switched and displayed, the tomographic images may be being recognized by the operator. On the other hand, after the tomographic images are displayed, in a case where the operator performs an operation for moving to the next imaging or an operation of instructing display of different images obtained by imaging, in many cases, recognition of the tomographic images is completed. In the sixth aspect, in a case where a predetermined operation is received after the tomographic images are displayed, the tomographic images are transmitted to the external apparatus. Therefore, it is possible to more reliably perform determination as to whether the tomographic image is visually recognized by the operator, as compared with the determination in the first aspect.

Figure 15:
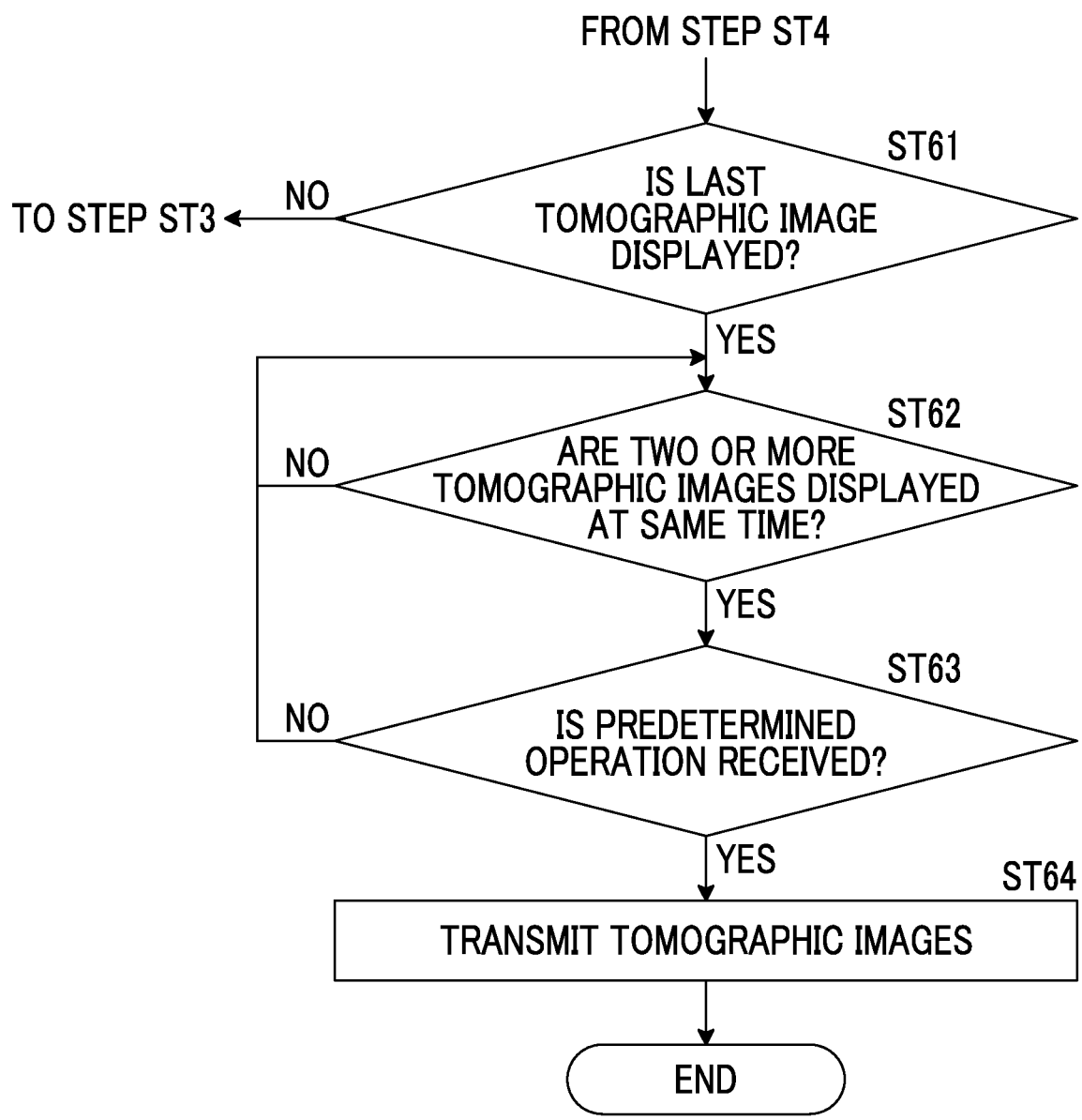
FIG. 15 is a flowchart illustrating processing in a case where determination according to a seventh aspect of the present embodiment is performed.

Next, processing in a case where the determination according to the seventh aspect is performed will be described. FIG. 15 is a flowchart illustrating processing in a case where the determination according to the seventh aspect of the present embodiment is performed. Following step ST4, the determination unit 34 determines whether or not the display control unit 33 displays the last tomographic image on the display unit 3 (step ST61). In a case where a determination result in step ST61 is NO, the process returns to step ST3, and then processing of step ST3 and subsequent steps is repeated.

In a case where a determination result in step ST61 is YES, the determination unit 34 further determines whether or not the display control unit 33 displays two or more tomographic images among the plurality of tomographic images on the display unit 3 at the same time according to an instruction of the operator (whether or not the display control unit 33 displays two or more tomographic images at the same time, step ST62). In a case where a determination result in step ST62 is NO, processing of step ST62 is repeated. In a case where a determination result in step ST62 is YES, the determination unit 34 determines whether or not a predetermined operation is received (step ST63). In a case where a determination result in step ST63 is NO, the process returns to step ST62. In a case where a determination result in step ST63 is YES, the transmission unit 35 transmits the plurality of generated tomographic images Dj to the external apparatus (step ST64), and processing is ended.

Thereby, in the seventh aspect, as in the first aspect, it is possible to reduce a waiting time from a time when imaging is completed to a time when the tomographic images can be read. Further, in a case where the plurality of tomographic images are only displayed at the same time, the tomographic images may be being recognized by the operator. On the other hand, after the tomographic images are displayed, in a case where the operator performs an operation for moving to the next imaging or an operation of instructing display of different images obtained by imaging, in many cases, recognition of the tomographic images is completed. In the seventh aspect, in a case where a predetermined operation is received after the tomographic images are displayed, the tomographic images are transmitted to the external apparatus. Therefore, it is possible to more reliably perform determination as to whether the tomographic image is visually recognized by the operator, as compared with the determination in the first aspect.

Figure 16:
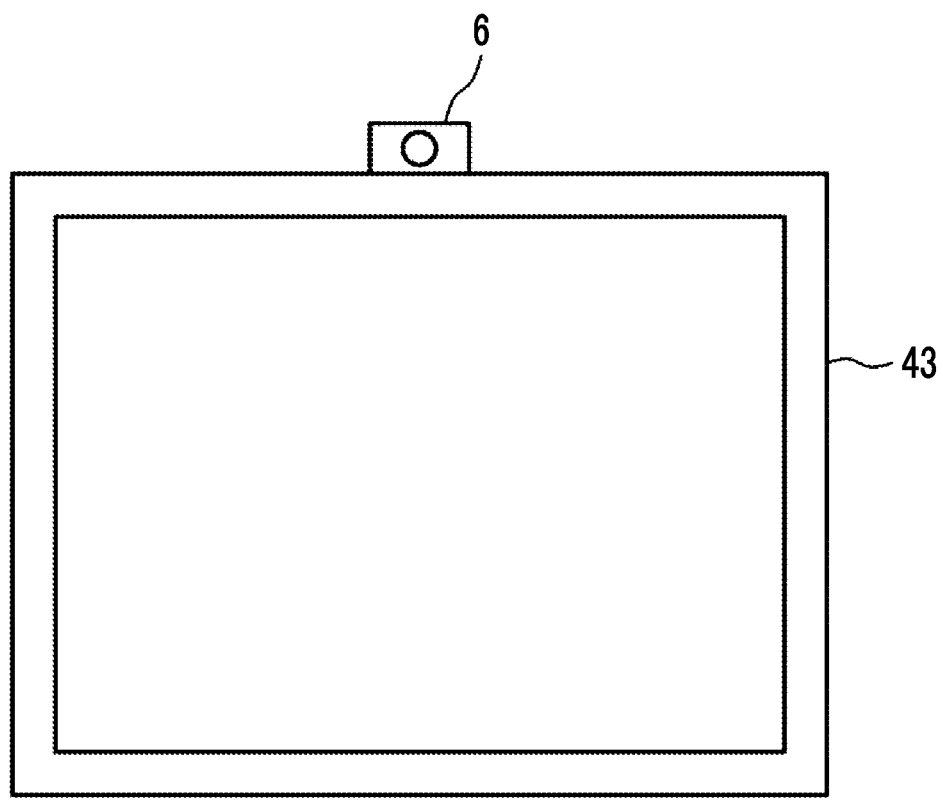
FIG. 16 is a diagram illustrating a display unit provided with a camera.

In the above embodiment, the determination unit 34 determines whether or not at least one tomographic image is visually recognized by the operator based on display of the tomographic images by the display control unit 33. On the other hand, the present disclosure is not limited thereto. For example, as illustrated in FIG. 16, in order to detect a line-of-sight of the operator looking at the display unit 3, the display unit 3 may include a camera 6 that acquires a moving image of the operator looking at the display unit 3 by imaging the operator. In this case, the determination unit 34 may detect a direction of the operator's eyes included in the moving image acquired by the camera 6 while the tomographic images are being displayed on the display unit 3. In a case where a certain time has passed while the direction of the eyes is facing the display unit 3, the determination unit 34 may determine that at least one tomographic image is visually recognized by the operator. In a state where the tomographic images are not displayed on the display unit 3, even in a case where a certain time has passed while the direction of the eyes is facing the display unit 3, the determination unit 34 does not determine that at least one tomographic image is visually recognized by the operator. Thereby, in a case where the tomographic images are not displayed on the display unit 3, it is possible to prevent the tomographic images from being transmitted to the external apparatus.

Further, in the embodiment, the image acquisition unit 31 acquires the projection images by causing the mammography apparatus 10 to perform imaging according to the imaging program. On the other hand, the present disclosure is not limited thereto. The plurality of projection images Gi may be acquired according to a program different from the imaging program, and may be stored in the storage 23 or an external storage device. In this case, the image acquisition unit 31 reads the plurality of projection images Gi from the storage 23 or the external storage device for reconfiguration processing or the like, the projection images Gi being stored in the storage 23 or the external storage device.

Further, the radiation in the embodiment is not particularly limited. For example, α-rays or γ-rays other than X-rays may be applied.

Further, in the embodiment, the subject is the breast M. On the other hand, the subject is not limited thereto. Any part of a human body such as a chest, an abdomen, a head, and limbs may be the subject.

Further, in the embodiment, for example, the following various processors may be used as a hardware structure of processing units performing various processing, such as the image acquisition unit 31, the reconfiguration unit 32, the display control unit 33, the determination unit 34, and the transmission unit 35. The various processors include, as described above, a CPU, which is a general-purpose processor that functions as various processing units by executing software (program), and a dedicated electric circuit, which is a processor having a circuit configuration specifically designed to execute a specific processing, such as a programmable logic device (PLD) or an application specific integrated circuit (ASIC) that is a processor of which the circuit configuration may be changed after manufacturing such as a field programmable gate array (FPGA).

One processing unit may be configured by one of these various processors, or may be configured by a combination of two or more processors having the same type or different types (for example, a combination of a plurality of FPGAs or a combination of a CPU and an FPGA). Further, the plurality of processing units may be configured by one processor.

As an example in which the plurality of processing units are configured by one processor, firstly, as represented by a computer such as a client and a server, a form in which one processor is configured by a combination of one or more CPUs and software and the processor functions as the plurality of processing units may be adopted. Secondly, as represented by a system on chip (SoC) or the like, a form in which a processor that realizes the function of the entire system including the plurality of processing units by one integrated circuit (IC) chip is used may be adopted. As described above, the various processing units are configured by using one or more various processors as a hardware structure.

Further, as the hardware structure of the various processors, more specifically, an electric circuit (circuitry) in which circuit elements such as semiconductor elements are combined may be used.

What is claimed is:

1. An image transmission apparatus comprising at least one processor, wherein the processor is configured to:
sequentially generate a plurality of tomographic images on each of a plurality of tomographic planes of a subject by reconfiguring a plurality of projection images corresponding to each of a plurality of radiation source positions, the plurality of projection images being generated by causing an imaging apparatus to perform tomosynthesis imaging of relatively moving a radiation source with respect to a detection surface of a radiation detector and irradiating the subject with radiation at the plurality of radiation source positions according to movement of the radiation source;

determine whether or not at least one of the tomographic images is visually recognized by an operator; and transmit the plurality of tomographic images to an external apparatus in a case where it is determined that at least one of the tomographic images is visually recognized by the operator.

2. The image transmission apparatus according to claim 1, wherein the processor is configured to transmit the plurality of tomographic images to the external apparatus before an instruction of completion of examination including the tomosynthesis imaging is input from the operator or before an instruction of transmission of the plurality of tomographic images to the external apparatus is input from the operator.

3. The image transmission apparatus according to claim 1, wherein, in a case where a simple two-dimensional image of the subject is acquired by simply imaging the subject with the same positioning as the tomosynthesis imaging, the processor is configured to transmit the plurality of tomographic images to the external apparatus before an instruction of completion of examination including the tomosynthesis imaging is input from the operator or before an instruction of transmission of the plurality of tomographic images to the external apparatus is input from the operator.

4. The image transmission apparatus according to claim 1, wherein the processor is configured to sequentially display, on a display, the tomographic images which are sequentially generated; and determine that at least one of the tomographic images is visually recognized by the operator in a case where the last tomographic image is displayed on the display.

5. The image transmission apparatus according to claim 1, wherein the processor is configured to sequentially display, on a display, the tomographic images which are sequentially generated; and determine that at least one of the tomographic images is visually recognized by the operator in a case where the last tomographic image is displayed on the display and a predetermined number of the tomographic images on the tomographic planes that are different from the last tomographic image are displayed on the display according to an instruction of the operator.

6. The image transmission apparatus according to claim 5, wherein the processor is configured to determine that at least one of the tomographic images is visually recognized by the operator in a case where the predetermined number of the tomographic images are displayed on the display and then a certain time has passed.

7. The image transmission apparatus according to claim 5, wherein the processor is configured to determine that at least one of the tomographic images is visually recognized by the operator in a case where the predetermined number of the tomographic images are displayed on the display and then a predetermined operation is received.

8. The image transmission apparatus according to claim 1, wherein the processor is configured to sequentially display, on a display, the tomographic images which are sequentially generated; and determine that at least one of the tomographic images is visually recognized by the operator in a case where the last tomographic image is displayed on the display and two or more tomographic images among the plurality of tomographic images are displayed on the display at the same time according to an instruction of the operator.

9. The image transmission apparatus according to claim 8, wherein the processor is configured to determine that at least one of the tomographic images is visually recognized by the operator in a case where two or more tomographic images among the plurality of tomographic images are displayed on the display at the same time and then a certain time has passed.

10. The image transmission apparatus according to claim 8, wherein the processor is configured to determine that at least one of the tomographic images is visually recognized by the operator in a case where two or more tomographic images among the plurality of tomographic images are displayed on the display at the same time and then a predetermined operation is received.

11. The image transmission apparatus according to claim 1, wherein the processor is configured to sequentially display, on a display, the tomographic images which are sequentially generated;
   detect a line-of-sight of the operator; and
   determine that at least one of the tomographic images is visually recognized by the operator in a case where it is detected that the operator looks at the display for a certain time while the tomographic images are being displayed on the display.

12. An image transmission method comprising:
   sequentially generating a plurality of tomographic images on each of a plurality of tomographic planes of a subject by reconfiguring a plurality of projection images corresponding to each of a plurality of radiation source positions, the plurality of projection images being generated by causing an imaging apparatus to perform tomosynthesis imaging of relatively moving a radiation source with respect to a detection surface of a radiation detector and irradiating the subject with radiation at the plurality of radiation source positions according to movement of the radiation source;
   determining whether or not at least one of the tomographic images is visually recognized by an operator; and
   transmitting the plurality of tomographic images to an external apparatus in a case where it is determined that at least one of the tomographic images is visually recognized by the operator.

13. A non-transitory computer-readable storage medium that stores an image transmission program causing a computer to execute:
   a procedure of sequentially generating a plurality of tomographic images on each of a plurality of tomographic planes of a subject by reconfiguring a plurality of projection images corresponding to each of a plurality of radiation source positions, the plurality of projection images being generated by causing an imaging apparatus to perform tomosynthesis imaging of relatively moving a radiation source with respect to a detection surface of a radiation detector and irradiating the subject with radiation at the plurality of radiation source positions according to movement of the radiation source;
   a procedure of determining whether or not at least one of the tomographic images is visually recognized by an operator; and
   a procedure of transmitting the plurality of tomographic images to an external apparatus in a case where it is determined that at least one of the tomographic images is visually recognized by the operator.

* * * * *